United States Patent
Delagrave et al.

(10) Patent No.: US 6,498,026 B2
(45) Date of Patent: Dec. 24, 2002

(54) VARIANT GALACTOSE OXIDASE, NUCLEIC ACID ENCODING SAME, AND METHODS OF USING SAME

(75) Inventors: Simon Delagrave, Avondale, PA (US); Anthony M. Maffia, III, Wilmington, DE (US); Dennis J. Murphy, Malvern, PA (US); Jennifer L. Rittenhouse Pruss, Atglen, PA (US); Edward J. Bylina, San Jose, CA (US); William J. Coleman, Mountain View, CA (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/782,906

(22) Filed: Feb. 14, 2001

(65) Prior Publication Data

US 2001/0051369 A1 Dec. 13, 2001

Related U.S. Application Data

(60) Provisional application No. 60/185,001, filed on Feb. 25, 2000.

(51) Int. Cl.$^7$ .......................... C12N 9/04; C12N 15/00; C07H 21/04

(52) U.S. Cl. ..................... 435/190; 435/440; 536/23.2

(58) Field of Search ................................ 435/190, 440; 536/23.2

(56) References Cited

U.S. PATENT DOCUMENTS

| | | | |
|---|---|---|---|
| 4,399,216 A | 8/1983 | Axel et al. ...................... | 435/6 |
| 4,683,195 A | 7/1987 | Mullis et al. ................... | 435/6 |
| 4,683,202 A | 7/1987 | Mullis ........................... | 435/91 |
| 4,879,236 A | 11/1989 | Smith et al. ................. | 435/235 |
| 5,502,091 A | 3/1996 | Dasgupta ..................... | 524/55 |
| 5,554,745 A | 9/1996 | Chiu et al. ................... | 536/52 |
| 6,022,717 A | 2/2000 | Brady et al. ................. | 435/101 |
| 6,090,604 A | 7/2000 | Golightly et al. ........... | 435/190 |

FOREIGN PATENT DOCUMENTS

| | | |
|---|---|---|
| EP | A-0367566 | 5/1990 |
| WO | WO 91/18982 | 12/1991 |
| WO | WO 93/11236 | 6/1993 |
| WO | WO 97/09433 | 3/1997 |

OTHER PUBLICATIONS

Reynolds et al. Tryosine 495 is a key residue in the active site of Galactose oxidase. Biochemical Society Transactions. (1995), 23(4), 510S.*
A. Baron et al., "Structure and Mechanism of Galactose Oxidase", The Journal of Biological Chemistry, vol. 269., No. 40 Issue of Oct. 7, 1994, pp. 25095–25105.
M. McPherson et al. "Galactose Oxidase of Dactylium dendroides", The Journal of Bilogical Chemistry, vol. 267, No. 12, Issue of Apr. 25, 1992, pp. 8146–8152.

S. Delagrave & D. Youvan, "Searching Sequence Space to Engineer Proteins: Exponential Ensemble Mutagenesis", Biotechnology vol. 11, Dec. 11, 1993, pp. 1548–1552.
Wm. PC Stemmer, "Rapid evolution of a protein in vitro by DNA shuffling", Nature, vol. 370, Aug. 4, 1994, pp. 389–391.
Aujame, L., et al., "High affinity human antibodies by phage display," Human Antibodies, 1997, 8(4), 155–168.
Ausubel et al. (Eds.), "Protocols in Molecular Biology," John Wiley & Sons, 1994.
Ausubel, et al. (Eds.), "Chapter 6, Screening of recombinant DNA libraries," Current Protocols in Molecular Biology, 1994, John Wiley & Sons, 6.0.1–6.4.10.
Bauer, et al., J. Biol. Chem., 1996, 271, 23749–23755.
Benoist, C., et al., "In vivo sequence requirements of the SV40 early promoter region," Nature, 1981, 290, 304–310.
Berger, et al., Guide to Molecular Cloning Techniques, Methods in Enzymology 152, Academic Press, 1987.
Bruggemann, M., et al., "Production of human antibody repertoires in transgenic mice," Curr. Opin. Biotechnol., 1997, 8, 455–458.
Bruggermann, M., et al., "Strategies for expressing human antibody repertoires in transgenic mice," Immunol. Today, 1996, 17(8), 391–397.
Carter, J.H., et al., "Validation of the galactose oxidase–schiff's reagent sequence for early detection and prognosis in human colorectal adenocarcinoma," Clin. Cancer Res., 1997, 3, 1479–1489.
Gathmann, W.D., et al., "Steric factors involved in the action of glycosidases and galactose oxidase," Biochem. Biophys. Res. Commun., 1981, 103, 68–76.
Chen, K., et al., "Enzyme engineering for nonaqueous solvents: random mutagenesis to enhance activity of subtilisin E in polar organic media," Biotechnology, 1991, 9, 1073–1077.
Chen, K., et al., "Tuning the activity of an enzyme for unusual environments: Sequential random mutagenesis of subtilisin E for catalysis in dimethylformamide," Proc. Natl. Acad. Sci. USA, 1993, 90, 5618–5622.
Cleveland, L., et al., "Superoxide dismutase activity of glactose oxidase," Biochim. Biophys. Acta, 1974, 341, 517–523.
Cosman, D., et al., "Cloning sequence and expression of human interleukin–2 receptor," Nature, 1984, 312, 768.
Cosman, D. et al., "High level stable expression of human interleukin–2 receptors in mouse cells generates only low affinity interleukin–2 binding sites, " Mol. Immunol., 1986, 23(9), 935–941.

(List continued on next page.)

Primary Examiner—Ponnathapua Achutamurthy
Assistant Examiner—Yong Pak
(74) Attorney, Agent, or Firm—Woodcock Washburn LLP

(57) ABSTRACT

The present invention provides mutant genes encoding variant galactose oxidase enzymes, termed vGOs; constructs and recombinant host cells incorporating the genes; the vGO polypeptides encoded by the genes; antibodies to the polypeptides; and methods of making and using all of the foregoing.

7 Claims, No Drawings

OTHER PUBLICATIONS

Cunningham, B.C., et al., "Improvement in the alkaline stability of subtilisin using an efficient random mutagenesis and screening procedure," *Protein Eng.* 1(4), 1987, 319–325.

Dayoff, M.O. in "Atlas of Protein Sequence and Structure," *National Biochemical Res. Foundation,*, Washington, D.C., vol. 5, 1972, 2 pages.

Delagrave, S., et al., "Searching sequence space to engineer proteins: exponential ensemble mutagenesis," *Bio/Technology*, 1993, 10, 1548–1552.

Eisenthal, R., et al. (Eds.), "Enzyme Assays: A Practical Approach," *Oxford University Press*, 1992.

Foote, J., et al., "Antibody franework residues affecting the conformation of thehypervariable loops," *J. Mol. Biol.*, 1992, 224, 487–499.

Harlow, et al. (Eds.), "Antibodies A Laboratory Manual," *Cold Spring Harbor Laboratory*, Cold Spring Harbor, New York, 1988.

Hendrix, R.W. (Ed.), "Lambda II," *Cold Spring Harbor Press*, Cold Spring Harbor, New York, 1980.

Hershey, A.D. (Ed.), "Lambda," *Cold Spring Harbor Press*, Cold Spring Harbor, New York, 1973.

Hoogenboom, H.R., "Designing and optimizing library selection strategies for generating high–affinity antibodies," *TIBTECH*, 1997, 15, 62–70.

Jones, P.T., et al., "replacing the complementarity–determining regions in a human antibody with those from a mouse," *Nature*, 1986, 321, 522–525.

Joo, H., et al., "A high–throughput digital imaging screen for the discovery and directed evolution of oxygenases," *Chem. & Biol.*, 1999, 6(10), 699–706.

Kettleborough, C.A., et al., "Humanization of a mouse monoclonal antibody by CDR–grafting; the importance of framework residues on loop conformation," *Protein Engin.*, 1991, 4(7), 773–783.

Lehninger, A.L., "Biochemistry," *Worth Publishers, Inc.*, New York, 1975, 71–77.

Leung, D.W., et al., "A method for random mutagenesis of a defined DNA segment using a modified polymerase chain reaction," *Technique–A J. Methods in Cell & Molecular Biology*, 1989, 1(1), 11–15.

Lis, M., et al., "Galactose oxidase–glucan binding domain fusion proteins as targeting inhibitors of dental plaque bacteria," *Antimicrobial Agents & Chemotherapy*, 1997, 41(5), 999–1003.

Luckow, V.A., et al., "High Level Expression of Nonfused Foreign Genes with Autographa californica Nuclear Polyhedrosis Virus Expression Vectors," *Virology*, 1989, *170*, 31–39.

Luckow, et al., "Trends in the development of baculovirus expression vectors," *Bio/Technology, Bio/Technology*, 1988, 6, 47.

Morrison, et al., "Genetically engineered antibody molecules," *Adv. Immunol.*, 1989, 44, 65–92.

O'Rielly, et al., (Eds.), "Baculovirus Expression Vectors: A Laboratory Manual," *W.H. Freeman and Company, New York*, 1992.

Okayama, H., et al., "A cDNA cloning vector that permits expression of a cDNA inserts in mammalian cells," *Mol. Cell. Biol.*, 1983, 3(2), 280–289.

Padlan, E.A., "A possible procedure for reducing the immunogenicity of antibody variable domains while preserving their ligand–binding properties," *Molecular Immunol.*, 1991, 28(4/5), 489–498.

Rader, C., et al., "Phage display of combinatorial antibody libraries," *Curr. Opin. Biotechnol.*, 1997, 8, 503–508.

Riechmann, L., et al., "Reshaping human antibodies for therapy," *Nature*, 1988, 332, 323–327.

Sambrook, et al., "Antibodies A Laboratory Manual," *Cold Spring Harbor Laboratory*, Cold Spring Harbor, New York, 1988.

Sambrook, et al. (Eds.), "Molecular Cloning: A Laboratory Manual," *Cold Spring Harbor Laboratory Press*, Cold Spring Harbor, New York, 1989.

Smith, T.F., et al., "Comparison of biosequences," *Adv. Appl. Math.*, 1981, 2, 482–489.

Smook, "Handbook for Pulp and Paper Technologists," *Canadian pulp and Paper Assn.*, 1982.

Stemmer, W.P.C., "Rapid evolution of a protein in vitro by DNA shuffling," *Nature*, 1994, 370, 389–391.

Summers, et al., A Manual of Methods for Baculovirus Vectors and Insect Cell Culture Procedures, *Texas Agricultural Experimental Station Bulletin No. 1555*, 1987, 3–46.

Tempest, P.R., et al., "Reshaping a human momoclonal antibody to inhibit human respiratory syncytial virus infection in vivo," *Bio/Technology*, 1991, 9, 266–271.

Verhoeyen, M., et al., "Reshaping human antibodies: grafting an antilysozyme activity," *Science*, 1988, 239, 1534–1536.

* cited by examiner

VARIANT GALACTOSE OXIDASE, NUCLEIC ACID ENCODING SAME, AND METHODS OF USING SAME

CROSS-REFERENCE TO RELATED APPLICATIONS

This application is related to U.S. Provisional Patent Application Ser. No. 60/185,001, filed Feb. 25, 2000, from which priority is claimed.

FIELD OF THE INVENTION

The present invention relates generally to the fields of genetics, cellular and molecular biology, and enzymology. More particularly, the invention relates to novel galactose oxidase enzymes, polynucleotides, and polypeptides.

BACKGROUND

The enzyme galactose oxidase (GO), encoded by the galactose oxidase gene (go) of *Dactylium dendroides* and other organisms, catalyzes a reaction in which a primary alcohol such as the C6 hydroxyl group of galactose is oxidized to an aldehyde with concomitant reduction of molecular oxygen to hydrogen peroxide, as shown generally in Formula I.

$$RCH_2OH + O_2 \rightarrow RCHO + H_2O_2 \qquad (I)$$

GO enzymes may be readily used to oxidize the D-galactose (and other hydroxyl-containing) side-chains of many complex compounds, including, but not limited to molecules comprising a D-galactose moiety that is not sterically hindered or blocked at the C6 hydroxyl, and molecules comprising a moiety such as dihydroxyacetone, glycerol, or similar short-chain alcohols in which a primary hydroxyl functional group is present. Of particular interest is the oxidation of guar gum. When guar gum is oxidized by GO, the resulting compound, called oxidized guar, can be used for many purposes, including use in paper manufacturing to add strength to paper products via the formation of acetal, hemiacetal, and other crosslinks with cellulose fibers (see, e.g., 1996; Aldehyde cationic derivatives of galactose containing polysaccharides used as paper strength additives; U.S. Pat. No. 5,554,745 (Chiu et al.); U.S. Pat. No. 5,502,091 (Dasgupta).

Galactose oxidases have been isolated from several species. For example, U.S. Pat. No. 6,090,604 discloses a genomic DNA sequence and deduced amino acid sequence for the GO enzyme from *Fusarium venenatum*.

Wildtype GO enzymes, however, are relatively inefficient oxidizers of guar gum and other compounds. Thus, there exists a need in the art for superior oxidizers of such compounds. Additionally, one obstacle to the development of variant GO's is the high viscosity of guar (e.g., the cationic guar used in this work has a viscosity of 1000 cps in 1% aqueous solution), a high molecular weight polymeric substrate. Indeed, many natural or synthetic polymers are insoluble or highly viscous when in solution, and are consequently difficult to pipette by hand or robotic means. Therefore, various methods of high-throughput screening used to evaluate such variant enzymes useful in adding functionality to viscous or insoluble polymers are needed by the art. Such methods enable those of skill in the art to create mutant GO enzymes capable of more efficient oxidative enzymatic reactions.

SUMMARY OF THE INVENTION

Although GO does display significant activity towards guar, the present inventors improved its specific activity via in vitro evolution of the enzyme. Using selected methods of mutagenesis, the present inventors created mutant galactose oxidase genes (mgo's) which encode variant galactose oxidase enzymes (vGO's), which variants are superior to wild-type GO in terms of efficiency of oxidizing guar and other compounds, as well as in conferring improved thermostability.

Error prone PCR (EPP) was used to generate mutant go genes, encoding variant GO enzymatic proteins. One of skill in the art will appreciate that any method capable of generating mutant genes would be suitable for practicing the present invention. In order to evaluate the efficiency of oxidation of the variants, certain recently developed methods of high throughput screening were used. However, one of skill in the art may choose a method of screening suitable to the substrate of interest. One aspect of the particular screening method used for the evolution of vGO's by the present inventors is the use of a proxy, i.e., a substrate that represents an adequate substitute for a problematic compound. Particularly, in order to evaluate vGO's oxidation of guar, the proxy methyl-α-D-galactose (methyl galactose) was used. The variant GO's of the present invention are demonstrably superior to wildtype GO in terms of their ability to oxidize guar and other complex compounds having hydroxyl-containing sidechains.

In one aspect, the present invention provides polynucleotides comprising mutant go genes. In another aspect, the invention provides polypeptides encoded by such polynucleotides. In another aspect, the invention provides variant GO enzymes having superior enzymatic activity (on methyl galactose or other substrates), and/or thermostability (i.e., resistance to heat inactivation), and which differ from wildtype GO by having at least one substituted amino acid. In another aspect, the present invention provides vectors comprising the polynucleotides. In another aspect, the present invention provides cells transfected or transformed with such vectors. In still another aspect, the present invention provides antibodies specific to the variant GOs. In another aspect, the present invention provides methods of using these molecules and constructs.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION OF THE INVENTION

The present invention provides purified and isolated polynucleotides (e.g., DNA sequences and RNA transcripts, both sense and complementary antisense strands, both single- and double-stranded, including splice variants thereof) encoding variant GO enzymes which differ from wildtype GO by at least one amino acid, and which exhibit superior enzymatic activity (on methyl galactose or other substrates) and/or thermostability. DNA polynucleotides of the invention include genomic DNA, cDNA, and DNA that has been chemically synthesized in whole or in part. The present invention also provides vectors comprising such polynucleotides, and cells transfected with such vectors. The present invention also provides the proteins encoded by such polynucleotides (i.e., variant GO enzymes), and methods of using the polynucleotides and polypeptides. The present invention also provides antibodies specific to vGOs capable of binding specifically to the variants while remaining unbound to wildtype GO.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. By the term "region" is meant a physically contiguous portion of the primary structure of a biomolecule. In the case of proteins, a region is defined by a contiguous portion of the amino acid sequence of that protein. The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region.

As used herein, the term "activity" refers to a variety of measurable indicia suggesting or revealing the extent of a catalytic reaction peformed by an enzyme, binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event. The term "better" activity, or "increased" activity, or "superior" activity, or the like, means an activity compared to the wildtype (and measured under the same conditions) that is at least about 10% higher, preferably at least about 25% higher, more preferably at least about 50% higher, more preferably at least about 75% higher, more preferably at least about 100% higher, more preferably at least about 1.35-fold higher, more preferably at least about 2-fold higher, more preferably at least about 3-fold higher, and most preferably at least about 4-fold higher. Such better, increased, or superior activity may be exhibited at particular desirable conditions of temperature, pressure, solution contents, and the like. Enzymatic activity of a GO enzyme may be measured using Vmax/Km, as described below in Example 1. A variant GO enzyme of the present invention has a Vmax/Km greater than 0.005 ΔOD405/min mM.

As used herein, the abbreviation in italicized lower case (go) refers to a gene, cDNA, RNA or nucleic acid sequence while the upper case version (GO) refers to a protein, polypeptide, peptide, oligopeptide, or amino acid sequence.

As used herein, the term "antibody" is meant to refer to complete, intact antibodies, and Fab, Fab', F(ab)2, and other fragments thereof. Complete, intact antibodies include monoclonal antibodies such as murine monoclonal antibodies, polyclonal antibodies, chimeric antibodies, and humanized antibodies.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to a small molecule, peptide, protein, sugar, nucleotide, or nucleic acid, and such compound may be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoded by the nucleic acid, or fragment thereof.

As used herein, the phrase "homologous nucleotide sequence," or "homologous amino acid sequence," or variations thereof, refers to sequences characterised by a homology, at the nucleotide level or amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding other known wildtype go genes. Homologous amino acid sequences include those amino acid sequences which encode conservative amino acid substitutions, as well as polypeptides having neuropeptide binding and/or signalling activity. A homologous amino acid sequence does not, however, include the amino acid sequence encoding other known wildtype GOs. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482–489, which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1–2-fold, and preferably more, compared to the basal level.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

The amino acid sequences are presented in the amino to carboxy direction, from left to right. The amino and carboxy groups are not presented in the sequence. The nucleotide sequences are presented by a single strand only, in the 5' to 3' direction, from left to right. Nucleotides and amino acids are represented in the manner recommended by the IUPAC-IUB Biochemical Nomenclature Commission, or (for amino acids) by three letters code, or by the accepted single letter code.

"Variant" GO (or vGO) enzymes are those which have a substitution of at least one amino acid, and have superior enzymatic activity and/or thermostability when compared with the wildtype enzyme. The enzymatic activity may be improved with regard to the substrate methyl galactose, but alternatively may be improved with regard to other substrates. The particular substitutions are described by indicating the one letter code for the wildtype amino acid, followed by the amino acid position, followed by the substituted amino acid in the variant. The position number is determined counting the first amino acid of the mature sequence, the mature sequence being defined by the crystal structure as number 1, with each consecutive amino acid numbered consecutively. The pre and prosequences are not included in the mature sequence. For example, the V494A variant describes a variant GO having the wildtype's valine at position 494 substituted with alanine. In cases where the wildtype's amino acid may be replaced with one of two or more amino acids, the variants are described by adding the additional single letter codes preceded by a slash (/); e.g., Y436N/H indicates a valine at position 494 substituted by either asparagine or histidine. Thus two distinct variants are described in this example, namely Y436N and Y436H.

A polynucleotide of the invention must have a mutation which renders at least one codon "nondegenerate", i.e., the codon must encode a different amino acid than the unmutated codon.

Genomic DNA of the invention comprises the protein coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a GO polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants which arise from in vitro manipulation). While allelic variants of wildtype GO are not encompassed by the present invention, those allelic variants which have been mutated and which encode variant GOs of the invention are within the scope of the invention.

The invention also comprehends cDNA that is obtained through reverse transcription of an RNA polynucleotide encoding vGO (conventionally followed by second strand synthesis of a complementary strand to provide a double-stranded DNA).

The wildtype GO nucleotide sequence is set forth in the following SEQ ID NO: I (gaoA, Genbank Accession No. M86819):

[SEQ ID NO: 1]
GAATTCGGCAGTGCCTGTGGATCCCAATGAGAGTTTCAACTAGTGGTGTCTTCACGACGCACTGCCGGAC

TCCGTCAGTCAATAGTTCAAGTTAGTTGGACGAACCGTTGGGCCGGTTGGTCACTAGACCAGGGACAATA

AGTGCAGACCAAGCTGCACACATCTTTGCCAAACCACTGTCCATGTCAGACCGAGCTGATATAATTTCAG

AAGCGAGTGACTCGGCTGCATCTTACTGCATTTATACGAGTCCTCCTCAGCTGTATTATATGATCTGAGT

GATCATATGCTCACTGGTCGCGTCCAATGGATAAATACTTCTGTCACGGTTTGCTTCTAAAGCGGTACCT

TGCAGATAGGCTGGCGGGTATGCAAGGACGGGCCTCGGCCATAAACTTTCAGCTCTGGACGCCACTTACT

GTATGTTGGTTATCGATCATCAGCGCACAGACAAATATCAGTGAATTGGTTCTCGTGATTTAAGTCTGGC

CGCCCTCTACGTCTAAGCGGCTTCAAATAACACGAACAGGCAATTTCGTTTCAACGCCACAAACATTTGG

GACCAATTAGACACCATTTTTAATTCATAGTTACTCCGAAAGAAGTTGAATCAGCTCATAATACAAACTA

GACAAGGTTGTCGGTGATTATTTGGCCCTGAAACGTGCAGCTTTTAAAACATGATCTTCCCGCAATGGCC

GATCAGCAAACGGTTCTTAGTGTATCCGTACCTGGATATATAAGACTGGAAGATATCAGTTACTCTTCAT

CTGCTAGTAAAACCTTCATCATCTTATCAAGTCATTCTCTACTAATTATTATCTCTCTTTATGTCAACAT

GAAACACCTTTTAACACTCGCTCTTTGCTTCAGCAGCATCAATGCTGTTGCTGTCACCGTCCCTCACAAG

GCCGTAGGAACTGGAATTCCTGAAGGGAGTCTTCAGTTCCTGAGCCTTCGAGCCTCAGCACCTATCGGAA

GCGCCATTTCTCGCAACAACTGGGCCGTCACTTGCGACAGTCCACAGTCGGGAAATGAATGCAACAAGGC

CATTGATGGCAACAAGGATACCTTTTGGCACACATTCTATGGCGCCAACGGGGATCCAAAGCCCCCTCAC

ACATACACGATTGACATGAAGACAACTCACAACGTCAACGGCTTGTCTATGCTGCCTCGACAGGATGGTA

ACCAAAACGGCTGGATCGGTCGCCATGAGGTTTATCTAAGCTCACATGGCACAAACTGGGGCAGCCCTGT

TGCGTCAGGTAGTTGGTTCGCCGACTCTACTACAAAATACTCCAACTTTGAAACTCGCCCTGCTCGCTAT

GTTCGTCTTGTCGCTATCACTGAAGCGAATGGCCAGCCTTGGACTAGCATTGCAGAGATCAACGTCTTCC

AAGCTAGTTCTTACACAGCCCCCCAGCCTGGTCTTGGACGCTGGGGTCCGACTATTGACTTACCGATTGT

TCCTGCGGCTGCAGCAATTGAACCGACATCGGGACGAGTCCTTATGTGGTCTTCATATCGCAATGATGCA

TTTGGAGGATCCCCTGGTGGTATCACTTTGACGTCTTCCTGGGATCCATCCACTGGTATTGTTTCCGACC

GCACTGTGACAGTCACCAAGCATGATATGTTCTGCCCTGGTATCTCCATGGATGGTAACGGTCAGATCGT

AGTCACAGGTGGCAACGATGCCAAGAACACCAGTTTGTATGATTCATCTAGCGATAGCTGGATCCCGGGA

CCTGACATGCAAGTGGCTCGTGGGTATCAGTCATCAGCTACCATGTCAGACGGTCGTGTTTTTACCATTG

GAGGCTCCTGGAGCGGTGGCGTATTTGAGAAGAATGGCGAAGTCTATAGCCCATCTTCAAAGACATGGAC

GTCCCTACCCAATGCCAAGGTCAACCCAATGTTGACGGCTGACAAGCAAGGATTGTACCGTTCAGACAAC

CACGCGTGGCTCTTTGGATCGAACAAGGGTTCGGTGTTCCAAGCGGGACCTAGCAGAGCCATGAACTGGT

ACTATACCAGTGGAAGTGGTCATGTGAAGTCAGCCGGAAAACGCCAGTCTAACCGTGGTGTAGCCCCTGA

TGCCATGTGCGGAAACGCTGTCATGTACGACGCCGTTAAAGGAAAGATCCTGACCTTTGGCGGCTCCCCA

GATTATCAAGACTCTGACGCCACAACCAACGCCCACATCATCACCCTCGGTGAACCCGGAACATCTCCCA

ACACTGTCTTTGCTAGCAATGGGTTGTACTTTGGCCGAACGTTTCACACCTCTGTTGTTCTTCCAGACGG

AAGCACGTTTATTACAGGAGGCCAACGACGTGGAATTCCGTTCGAGGATTCAACCCCGGTATTTACACCT

GAGATCTACGTCCCTGAACAAGACACTTTCTACAAGCAGAACCCCAACTCCATTGTTCGCGTCTACCATA

GCATTTCCCTTTTGTTACCTGATGGCAGGGTATTTAACGGTGGTGGTGGTCTTTGTGGCGATTGTACCAC

GAATCATTTCGACGCGCAAATCTTTACGCCAAACTATCTTTACAATAGCAACGGCAATCTCGCGACACGT

CCCAAGATTACCAGAACCTCTACACAGAGCGTCAAGGTCGGTGGCAGAATTACAATCTCGACGGATTCTT

CGATTAGCAAGGCGTCGTTGATTCGCTATGGTACAGCGACACACACGGTTAATACTGACCAGCGCCGCAT

TCCCCTGACTCTGACAAACAATGGAGGAAATAGCTATTCTTTCCAAGTTCCTAGCGACTCTGGTGTTGCT

-continued

```
TTGCCTGGCTACTGGATGTTGTTCGTGATGAACTCGGCCGGTGTTCCTAGTGTGGCTTCGACGATTCGCG

TTACTCAGTGATTTGTTAGGAAGCCAAGTTTCATAGGATATTGTTCTACTCAGCGATCGGTCAATTTAAT

TTACTGCCCTGTTTACTTGAAGTAGTCGTCGCTGTAAAGGGTCGCCGTGTACTCTTTCTGGTTGAGTCAA

CTCGTGGTCCGTCCGGTCACTCTGCCTGTGACCCAGCTGAAGACTACCAGAAAGAAGACTTCAAACGTAT

TTCAGTCTAGCAACAGCGCCAAGAAGCTCGCTGTCAAAAGTGCCGGTGGCGTTTATCGTGAATCGATAGT

TTGACGGCCTTACTCGCCTCTGGTGTAGCTGGAAAAGCATCAACCATCCGGCCCAATCACGAGAATGACG

TCAATGGCTGTGAGTGATGATACTAACTGAAAATGGTAATTCAACTGACGATGGAGCGTTGACATGCTAA

TCGGTCTCGATCATCAACAGCAGTAAGGAGCTTGACGGTTTGTGCTCTGTTGATCATCAGATGATGTGGT

GTTCCTGCAGTAGATGCACAAGGCCAGGAAAAGAAGTAAAGCCACTTTGTCTACCAATCGGTTGGGATGC

GGTGAGATCTCAAGGGAATGGGTTCAAGAGTCTAGA
```

The corresponding amino acid sequence for the mature wildtype GO is set forth in the following SEQ ID NO: 2.

[SEQ ID NO: 2]
ASAPIGSAISRNNWAVTCDSAQSGNECNKAIDGNKDTFWETFYGANGDPKPPHTYTIDMKTTQNVNGLSM

LPRQDGNQNGWIGRHEVYLSSDGTNWGSPVASGSWFADSTTKYSNFETRPARYVRLVAITEANGQPWTSI

AETNVFQASSYTAPQPGLGRWGPTIDLPIVPAAAAIEPTSCRVLMWSSYRNDAFGGSPGGTTLTSSWDPS

TGTVSDRTVTVTKHDMFCPGTSMDGNGQIVVTGGNDAKKTSLYDSSSDSWIPGPDMQVARGYQSSATMSD

GRVFTIGGSWSGGVFEKNGEVYSPSSKTWTSLPNAKVNPMLTADKQGLYRSDNHAWLFGWKKGSVFQAGP

STAMNWYYTSGSGDVKSAGKRQSNRGVAPDAMCGNAVMYDAVKGKILTFGGSPDYQDSDATTNAHIITLG

EPGTSPNTVFASNGLYFARTFHTSVVLPDGSTFITGGQRRGIPFEDSTPVFTPEIYVPEQDTFYKQNPNS

IVRVYHSISLLLPDGRVFNGGGGLCGDCTTNHFDAQIFTPNYLYNSNGNLATRPKTTRTSTQSVKVGGRT

TISTDSSISKASLIRYGTATHTVNTDQRRTPLTLTNNGGNSYSFQVPSDSGVALPGYWMLFVMNSAGVPS

VASTIRVTQ

The sequence for the precursor protein, which includes the signal sequence and prosequence, may be found in Genbank Accession No. Q01745.

Several preferred DNA sequences of a mgo encoding a vGO polypeptide of the invention having superior enzymatic activity compared to wildtype are those which encode a variant GO having a substitution at any of positions C383, Y436, V494, and Q63. More preferably, the preferred polynucleotide encodes a variant GO having more than one of these preferred substitutions. More preferably, the polynucleotide encodes a variant GO having at least one of the substitutions selected from the group consisting of C383S, V494A, Q63K, and either Y436N or Y436H, more preferably at least two of those substitutions, more preferably at least three of those substitutions. A preferred DNA of the invention comprises a double stranded molecule along with the complementary molecule (the "non-coding strand" or "complement") having a sequence unambiguously deducible from the coding strand according to Watson-Crick base-pairing rules for DNA. These preferred examples are illustrative; the invention embraces other variants which have additional substitutions, and the polynucleotides that encode such variants, provided such variants have superior activity.

Several preferred DNA sequences of a mgo encoding a vGO polypeptide of the invention having superior enzymatic activity compared to wildtype are those which encode a variant GO having a substitution at any of positions G195, S553, G6, Q238, K342, N427, and Q63. More preferably, the preferred polynucleotide encodes a variant GO having more than one of these preferred substitutions. More preferably, the polynucleotide encodes a variant GO having at least one of the substitutions selected from the group consisting of S553C, G6R, Q238L, K342E, N427T, Q63K, and either G195A or G195E, more preferably at least two of those substitutions, more preferably at least three of those substitutions. In a preferred embodiment of the invention, the polynucleotide encodes a variant GO having at least one substitution conferring superior enzymatic activity and at least one substitution conferring superior thermostability. A preferred DNA of the invention comprises a double stranded molecule along with the complementary molecule (the "non-coding strand" or "complement") having a sequence unambiguously deducible from the coding strand according to Watson-Crick base-pairing rules for DNA. These preferred examples are illustrative; the invention embraces other variants which have additional substitutions, and the polynucleotides that encode such variants, provided such variants have superior thermostability. Preferred polypeptides include all those encoded by the preferred DNA sequences as described above.

The invention further embraces species homologs of the mgo DNA. For example, species homologs have been found in *Gibberella fujikuroi, Polyporus circinatus, Arabidopsis*

*thaliana* (CAB65567), and *Streptomyces coelicolor* A3(2) (CAB41193), among others. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with DNA of the invention. Generally, percent sequence "homology" with respect to polynucleotides of the invention may be calculated as the percentage of nucleotide bases in the candidate sequence that are identical to nucleotides in the preferred polynucleotides discussed above, after aligning the sequences and introducing gaps, if necessary, to achieve the maximum percent sequence identity.

The polynucleotide sequence information provided by the invention makes possible large-scale expression of the encoded polypeptide by techniques well known and routinely practiced in the art. Polynucleotides of the invention also permit identification and isolation of polynucleotides encoding related vGO polypeptides, such as human allelic variants and species homologs, by well-known techniques including Southern and/or Northern hybridization, and polymerase chain reaction (PCR). Examples of related polynucleotides include human and non-human genomic sequences, including allelic variants, as well as polynucleotides encoding polypeptides homologous to vGO and structurally related polypeptides sharing one or more biological, enzymatic, immunological, and/or physical properties of vGO. Non-human species genes encoding proteins homologous to vGO can also be identified by Southern and/or PCR analysis. Knowledge of the sequence of a human mgo DNA also makes possible through use of Southern hybridization or polymerase chain reaction (PCR) the identification of genomic DNA sequences encoding vGO expression control regulatory sequences such as promoters, operators, enhancers, repressors, and the like. Polynucleotides of the invention are also useful in hybridization assays to detect the capacity of cells to express vGO.

The disclosure herein of a full-length polynucleotide encoding a vGO polypeptide makes readily available to the worker of ordinary skill in the art every possible fragment of the full length polynucleotide which contains a mutation encoding the variant amino acid. The invention therefore provides fragments of vGO-encoding polynucleotides comprising at least 14, and preferably at least 16, 18, 20, 25, 50, or 75 consecutive nucleotides of a polynucleotide encoding vGO, provided that the fragment contains the mutated nucleotide codon. Polynucleotide fragments of genomic sequences of the invention comprise not only sequences unique to the coding region, but also may include fragments of the full-length sequence derived from introns, regulatory regions, and/or other non-translated sequences. Sequences unique to polynucleotides of the invention are recognizable through sequence comparison to other known polynucleotides (e.g., the wildtype), and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragment mgo polynucleotides. One or more polynucleotides can be included in kits that are used to detect the presence of a polynucleotide encoding vGO, or used to detect variations in a polynucleotide sequence encoding vGO.

The invention also embraces DNAs encoding vGO polypeptides that hybridize under moderately stringent or high stringency conditions to the non-coding strand, or complement, of the preferred polynucleotides set forth above.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1× SSC and 1% SDS. It is understood in the art that conditions of equivalent stringency can be achieved through variation of temperature and buffer, or salt concentration as described Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Autonomously replicating recombinant expression constructs such as plasmid and viral DNA vectors incorporating polynucleotides of the invention are also provided. Expression constructs wherein vGO-encoding polynucleotides are operatively linked to an endogenous or exogenous expression control DNA sequence and a transcription terminator are also provided. Expression control DNA sequences include promoters, enhancers, operators, and regulatory element binding sites generally, and are typically selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but may also be utilized simply to amplify a vGO-encoding polynucleotide sequence.

According to another aspect of the invention, host cells are provided, including prokaryotic and eukaryotic cells, comprising a polynucleotide of the invention (or vector of the invention) in a manner which permits expression of the encoded vGO polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cells systems.

Host cells of the invention are a valuable source of immunogen for development of antibodies specifically immunoreactive with a vGO of the present invention. Host cells of the invention are also useful in methods for the large-scale production of vGO polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of mgo DNA sequences allows for modification of cells to permit, or increase, expression of endogenous vGO. Cells can be modified (e.g., by homologous recombination) to provide increased expression by replacing, in whole or in part, the naturally occurring mgo promoter with all or part of a heterologous promoter so that the cells express vGO at higher levels. The heterologous promoter is inserted in such a manner that it is operatively linked to endogenous vGO encoding sequences. It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the mgo coding sequence, amplification of the marker DNA by standard selection methods results in co-amplification of the mgo coding sequences in the cells.

The invention also provides purified and isolated vGO polypeptides encoded by a polynucleotide of the invention. Presently preferred are vGO polypeptides comprising at least one substitution at any of the positions S553, G6, Q238, K342, N427, Q63, and G195. More preferably, the vGO enzyme has a combination of substitutions, and more preferably the substitutions are selected from the group consisting of S553C, G6R, Q238L, K342E, N427T, Q63K, and either G195A or G195E.

The invention also embraces polypeptides that have at least 99%, at least 95%, at least 90%, at least 85%, at least 80%, at least 75%, at least 70%, at least 65%, at least 60%, at least 55% or at least 50% identity and/or homology to the preferred polypeptide of the invention, provided that the sequence has at least the amino acid variations present in any of the preferred polypeptides set forth above. Percent amino acid sequence "identity" with respect to the preferred polypeptide of the invention is defined herein as the percentage of amino acid residues in the candidate sequence that are identical with the residues in the vGO sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the vGO sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment (Dayhoff, in *Atlas of Protein Sequence and Structure*, Vol. 5, p. 124, National Biochemical Research Foundation, Washington, D.C. (1972), incorporated herein by reference).

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of vGO polypeptides are embraced by the invention.

The invention also embraces variant (or analog) vGO polypeptides. In one example, insertion variants are provided wherein one or more amino acid residues supplement a vGO amino acid sequence. Insertions may be located at either or both termini of the protein, or may be positioned within internal regions of the vGO amino acid sequence. Insertional variants with additional residues at either or both termini can include, for example, fusion proteins and proteins including amino acid tags or labels.

Insertion variants include vGO polypeptides wherein one or more amino acid residues are added to a vGO amino acid sequence, or to an enzymatically active fragment thereof.

Other products of the invention also include mature vGO products, i.e., vGO products wherein leader or signal sequences are removed, with additional amino terminal residues. The additional amino terminal residues may be derived from another protein, or may include one or more residues that are not identifiable as being derived from specific proteins. vGO products with an additional methionine residue at position −1 (Met$^{-1}$-vGO) are contemplated, as are variants with additional methionine and lysine residues at positions −2 and −1 (Met$^{-2}$-Lys$^{-1}$-vGO). Variants of vGO with additional Met, Met-Lys, Lys residues (or one or more basic residues in general) are particularly useful for enhanced recombinant protein production in bacterial host cells.

The invention also embraces vGO variants having additional amino acid residues which result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino terminus and/or the carboxy terminus of vGO is/are fused to another polypeptide.

In another aspect, the invention provides deletion variants wherein one or more amino acid residues in a vGO polypeptide are removed. Deletions can be effected at one or both termini of the vGO polypeptide, or with removal of one or more non-terminal amino acid residues of vGO. Deletion variants, therefore, include all fragments of a vGO polypeptide.

The invention thus embraces polypeptide fragments of the preferred vGO polypeptides set forth above, wherein the fragments maintain enzymatic properties of a vGO polypeptide, provided the fragments contain the substituted amino acid(s) distinguishing the vGO polypeptide from the wildtype. Such fragments comprising at least 5, 10, 15, 20, 25, 30, 35, or 40 consecutive amino acids of are comprehended by the invention. Preferred polypeptide fragments display antigenic properties unique to, or specific for, human vGO and its allelic and species homologs. Fragments of the invention having the desired enzymatic properties can be prepared by any of the methods well known and routinely practiced in the art.

In still another embodiment, the invention provides substitution variants of vGO polypeptides. Substitution variants include those polypeptides wherein one or more amino acid residues of a vGO polypeptide are removed and replaced with alternative residues, provided the substitution variants contain the variant amino acid(s) distinguishing the vGO polypeptide from the wildtype. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

Conservative Substitutions I

| SIDE CHAIN CHARACTERISTIC | AMINO ACID |
|---|---|
| Aliphatic | |
| Non-polar | G A P<br>I L V |
| Polar - uncharged | C S T M<br>N Q |
| Polar - charged | D E<br>K R |
| Aromatic | H F W Y |
| Other | N Q D E |

Alternatively, conservative amino acids can be grouped as described in Lehninger, (*Biochemistry*, Second Edition; Worth Publishers, Inc. NY, N.Y. (1975), pp.71–77) as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells. Similarly, the invention further embraces vGO polypeptides that have been covalently modified to include one or more water-soluble polymer attachments such as polyethylene glycol, polyoxyethylene glycol, or polypropylene glycol. Variants that display enzymatic properties of vGO and are expressed at higher levels are also contemplated.

In a related embodiment, the present invention provides compositions comprising purified polypeptides of the invention. Preferred compositions comprise, in addition to the polypeptide of the invention, an acceptable liquid, semisolid, or solid diluent that serves as a vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

With the knowledge of the nucleotide sequence information disclosed in the present invention, one skilled in the art can identify and obtain nucleotide sequences which encode vGOs from different sources (i.e., different tissues or different organisms) through a variety of means well known to the skilled artisan and as disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

A nucleic acid molecule comprising any of the vGO nucleotide sequences described above may be obtained using any means of mutagenesis performed on the wildtype go sequence. Such methods include error prone PCR, use of mutagenic strains such as the XL1-Red mutator strain of *E. coli* (Stratagene Inc.), use of random mutagenesis methods involving mutagenic chemicals such as ethyl-methyl sulfonate (EMS) or involving irradiation by UV light or other radiations of higher or lower energy, combinatorial cassette mutagenesis (Delagrave, et al., (1993), *Bio/Technology*, 10, 1548–52), site-directed mutagenesis, mutagenesis by PCR involving the incorporation of one or more primers encoding mutations, mutagenesis by DNA shuffling (e.g., Stemmer, 1994, Nature, 370:389, and other closely related methods), and mutagenesis by any PCR method.

A nucleic acid molecule comprising any of the vGO nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. PCR provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, Methods in Enzymology 152 Academic Press, Inc., San Diego, Calif. (Berger), which is incorporated herein by reference in its entirety.

Another aspect of the present invention is directed to vectors, or recombinant expression vectors, comprising any of the nucleic acid molecules described above. Vectors are used herein either to amplify DNA or RNA encoding vGO and/or to express DNA which encodes vGO. Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxviruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT vectors, pGEM vectors (Promega), pPROEXvectors (LTI, Bethesda, Md.), Bluescript vectors (Stratagene), pQE vectors (Qiagen), pSE420 (Invitrogen), and pYES2 (Invitrogen).

Preferred expression vectors are replicable DNA constructs in which a DNA sequence encoding vGO is operably linked or connected to suitable control sequences capable of effecting the expression of the vGO in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding, and sequences which control the termination of transcription and translation.

Preferred vectors preferably contain a promoter that is recognised by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacz promoters of *E. coli* and the SV40 early promoter (Benoist, et al. *Nature*, 1981, 290, 304–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgamo of the replicase gene of the phage MS-2 and of the gene cII of bacteriophage lambda. The Shine-Dalgarno sequence may be directly followed by DNA encoding vGO and result in the expression of the mature vGO protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and vGO DNA. An example of a suitable marker is dihydrofolate reductase (DHFR) or thymidine kinase (see, U.S. Pat. No. 4,399,216).

Nucleotide sequences encoding vGO may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.,* 1983, 3, 280, Cosman et al., *Mol. Immunol.,* 1986, 23, 935, Cosman et al., *Nature,* 1984, 312, 768, EP-A-0367566, and WO 91/18982, each of which is incorporated herein by reference in its entirety.

Another embodiment of the present invention is directed to transformed host cells having an expression vector comprising any of the nucleic acid molecules described above. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera Escherichia, Bacillus, Salmonella, Pseudomonas, Streptomyces, and Staphylococcus.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera Saccharomyces, Pichia, and Kluyveromyces. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology,* 1988, 6, 47, Baculovirus Expression Vectors: A Laboratory Manual, O'Rielly et al. (Eds.), W. H. Freeman and Company, New York, 1992, and U.S. Pat. No. 4,879,236, each of which is incorporated herein by reference in its entirety). In addition, the MAX-BAC™ complete baculovirus expression system (Invitrogen) can, for example, be used for production in insect cells.

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for vGO or fragments thereof. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind vGO polypeptides exclusively (i.e., are able to distinguish vGO polypeptides from other known vGO polypeptides by virtue of measurable differences in binding affinity, despite the possible existence of localized sequence identity, homology, or similarity between vGO and such polypeptides). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), *Antibodies A Laboratory Manual;* Cold Spring Harbor Laboratory; Cold Spring Harbor, N.Y. (1988), Chapter 6. Antibodies that recognize and bind fragments of the vGO polypeptides of the invention are also contemplated, provided that the antibodies are specific for vGO polypeptides. Antibodies of the invention can be produced using any method well known and routinely practiced in the art.

Non-human antibodies may be humanized by any of the methods known in the art. In one method, the non-human CDRs are inserted into a human antibody or consensus antibody framework sequence. Further changes can then be introduced into the antibody framework to modulate affinity or immunogenicity. Antibodies of the invention are useful for, e.g., detecting or quantifying vGO, as well as purifying vGO. Kits comprising an antibody of the invention for any of the purposes described herein are also comprehended. In general, a kit of the invention also includes a control antigen for which the antibody is imnuunospecific.

In other embodiments of the invention, the polypeptides of the invention are employed as a research tool for identification, characterization and purification of interacting, regulatory proteins. Appropriate labels are incorporated into the polypeptides of the invention by various methods known in the art and the polypetides are used to capture interacting molecules. For example, molecules are incubated with the labeled polypeptides, washed to removed unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors of GO, such as 6-thio-methyl-galactose identified as an inhibitor by Wachter et al., 1996, Biochemistry 35:14425 –14435, and others. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

The vGO enzyme may be used to oxidize compounds, such as, for example, hydroxyl containing compounds, provided that the group to be oxidized is available (e.g., sterically) for the enzyme to carry out its oxidation function. A group available to the enzyme in this regard is referred to herein as free of steric hindrance. Steric factors involved in the GO enzyme's action are discussed generally in Cathmann et al., 1981, Biochem. Biophys. Res. Commun. 103:68–76, the disclosure of which is hereby incorporated by reference in its entirety. Examples of compounds for which vGO may be used to perform oxidation, and wherein the vGO may have improved enzymatic activity, include, but are not limited to, galactose, lactose, raffinose, dihydroxyacetone, diethylene glycol, ethanol and other primary alcohols, and guaran gums, D-galacto-hexodialdose, dihydroxyacetone, 3-hydroxy-2-oxo-propionaldehyde, glycerol, S(−)-glyceraldehyde, 6"-carboxyraffinose, methyl-alpha-D-galactopyranose, methyl-beta-D-galactopyranose, major glycolipid of human red cells, D-talose, 3-halo-1,2-propane-diols, GM1 ganglioside, D-galactosamine, melibiose, stachyose, desialyated glycoproteins (e.g., fetuin, mucin), N-acetyl-D-galactosamine, isopropyl-beta-D-thiogalactosylpyranoside, beta-thiodigalactoside, melibiitol, melibionic acid, 1,5-anhydrogalactitol, planteose, 2-glycerol-alpha-D-galactopyranoside, galactobiose, beta-D-galactopyranosyl, beta-D-galactopyranosyl, D-glucose, methyl-beta-D-thiogalactosylpyranoside, and the like. The GO enzyme has also been characterized as possessing activity as a superoxide dismutase (Cleveland et al., 1974, Biochim. Biophys. Acta 341:517–523).

For example, the oxidation of guar may be performed on a 1% guar mixture in pH 7 phosphate buffer containing galactose oxidase, catalase, and horse radish peroxidase. The reaction may be run at 26° C. with constant mixing and sparging with air for approximately 3 hours. Suitable reaction conditions are set forth, for example, in U.S. Pat. No. 6,022,717, the disclosure of which is hereby incorporated herein by reference in its entirety.

The oxidized compounds resulting from interaction with the variant GO enzymes of the invention are useful in a wide variety of applications and chemical processes that will be readily apparent to those of skill in the art. Oxidized guar, for example, may be used in papermaking processes, such as those described generally in Smook, Handbook for Pulp and Paper Technologists (Canadian Pulp and Paper Assn. 1982), which is hereby incorporated by reference in its entirety.

Using the variants of the invention, one of skill in the art may more efficiently oxidize guar gum for use in, for example, a method of making paper. The variant enzyme is isolated in sufficient quantity, then used to oxidize guar gum, and the oxidized guar is added to the paper pulp during the paper-making process. More detailed descriptions of such papermaking processes may be found in U.S. Pat. No. 6,022,717.

There are many other possible uses of the variants of the invention, including, but not limited to, generation of $H_2O_2$ in situ; enzymatic synthesis of other aldehydes; pulp biobleaching; the use of galactose oxidase-Schiff's reagent for early detection and prognosis in human colorectal adenocarcinoma (e.g., Carter et al., Clin Cancer Res 1997 September; 3(9):1479–89); and the use of galactose oxidase-glucan binding domain fusion proteins as targeting inhibitors of dental plaque bacteria (Lis & Kurimitsu. Antimicrob Agents Chemother 1997 May; 41(5):999–1003). Those of skill in the art will readily appreciate the many uses to which a galactose oxidase enzyme may be put.

Additional features of the invention will be apparent from the following Examples. Example 1 is actual, while the remaining Examples are prophetic.

EXAMPLE 1

In vitro Evolution of Variant Galactose Oxidase Enzymes

Plasmid pGAO11 encoding the entire gaoA open-reading-frame (GenBank accession number M86819), as well as a rat anti-GO polyclonal antibody were kindly provided by Prof. McPherson of Leeds University, UK. Enzymes were obtained from Roche Molecular Biochemicals (Indianapolis, Ind.), New England Biolabs (Beverly, Mass.) and Sigma (St-Louis, Mo.). Oligonucleotides were synthesized by Operon (Alameda, Calif.). Kits from Qiagen (Valencia, Calif.) were used for plasmid DNA preparation and extraction. DH10B competent cells were purchased from Life Technologies (Grand Island, N.Y.). The pBADmyc/his E. coli expression vector was obtained from Invitrogen (Carlsbad, Calif.).

Molecular biology techniques described in Sambrook et al., supra, were generally followed. The pBADmyc/his vectors were used for recombinant expression of GO in E. coli. The entire GO orf was subcloned into pBADmyc/his by digesting an overlap PCR product with Sph I and Hind III and ligating this DNA fragment to similarly digested vector DNA. A silent Xho I restriction site at the 5' end of the GO orf and a Hind III site immediately after two engineered stop codons were introduced by the oligos used for overlap PCR. The resulting construct, in which the GO orf was not in frame with the C-terminal myc/his tag provided by the vector, was designated pBADGO6. A silent Kpn I site was engineered into pBADGO6 to yield clone pBADGOK3. This latter construct was used as a wildtype control (WT) in subsequent experiments. The GO orfs of both plasmids were sequenced completely.

A. Expression of GO in E. coli

The entire GO open reading frame was thus subdloned into the inducible E. coli expression vector as a necessary first step for mutagenesis and high-throughput screening. A 64 kDa polypeptide corresponding to GO protein was detected by SDS-PAGE and anti-GO western blotting in liquid cultures of the recombinant GO clone. Induction at 26° C. for about four hours was needed to produce measurable GO activity. Addition of $CuSO_4$ (0.33 to 1 mM) to the induction medium was also necessary to achieve measurable amounts of GO activity in recombinant cultures. This copper requirement is consistent with the presence of $Cu^{2+}$ in the enzyme active site.

B. Very High Throughput Screening

Many assays can be used to examine enzymatic activity including, but not limited to, photometric, radiometric, HPLC, electrochemical, and the like, which are described in, for example, Enzyme Assays: A Practical Approach, eds. R. Eisenthal and M. J. Danson, 1992, Oxford University Press, which is incorporated herein by reference in its entirety. In this case, however, to detect GO activity, a coupled assay was devised which would generate a colored and, ideally, insoluble product. Hydrogen peroxide, produced by GO when it oxidizes a substrate, is used by a peroxidase in the coupled assay to transform 4-chloro-naphthol (4CN) into an insoluble colored product. The insoluble colored product absorbs visible light maximally at 550 nm. Because guar comprises galactose side-chains in a 1–6 linkage with a poly-mannose backbone, methyl-galactose is an appropriate proxy for guar. Although this assay can be performed in liquid phase using cell lysates, the present invention uses a screening method that does not require the extensive robotic infrastructure of typical liquid-phase high throughput systems, while at the same time significantly improving throughput. It does so by combining a solid phase assay with digital imaging technology.

In one embodiment, approximately four to five thousand bacterial microcolonies (each less than 1 mm in size) can be grown and induced on a single porous membrane and subsequently exposed to chloroform vapor to lyse the bacterial cells. The membrane is then transferred to the surface of an assay plate comprising an agarose gel to synchronously initiate the chromogenic enzyme reactions in the microcolonies. The gel contains methyl-galactose, cupric sulfate, potassium phosphate buffer, 4CN and soybean peroxidase as described in the protocols below. The resulting assay plate is immediately inserted into a 'Kcat' instrument, also known as the MicroColonyImager as described in U.S. Pat. No. 5,914,245. Alternatively, the assay plate is prewarmed in the Kcat instrument, and the membrane is transferred to the surface of the assay plate while it is in the instrument.

In one embodiment, the Kcat instrument periodically captures a digital image of the membrane illuminated at a specified wavelength. Color develops in the microcolonies as a result of GO activity and the stored digital images are used to compute an absorbance vs. time plot for each pixel in the image. The kinetic data associated with each pixel can be displayed, compared and sorted to determine rapidly which mutant microcolony on the assay plate is most active.

The reaction rate of GO in bacterial colonies, as indicated by transformation of 4CN into an insoluble colored compound, was roughly linear in the first 5–10 minutes after transfer of the microcolony-bearing membrane to the assay plate. As a result, at least four membranes (a total of 15,000 to 20,000 mutants) can be screened in one hour using a single instrument while still allowing adequate time for analysis of the data. At this rate, 80,000 mutants can easily be screened in a single day, which is an order of magnitude greater than in typical robotic high-throughput screens. Moreover, there is no need for coexpression of a peroxidase (Joo et al., 1999, *Chem. & Biol.* 6, 699–706, 1999) because it is simply added to the assay medium. Since the assay and instrumentation rely on a simple colorimetric reaction, the methodology or variations thereof are applicable to a wide range of different enzymes and chemistries.

In one embodiment, the assay is performed as follows:

Day 1:

Transformations:

Electroporation was used to produce *E. coli* cells expressing mutant libraries of GO. One microliter of DNA (for example, DNA of mutant libraries whose construction is described in section C on directed evolution below) is transformed into 30 microliters of electro-competent cells (DH10B electro-competent cells from Life Technologies) using a Gene Pulser (BioRad). Methods of transforming DNA into biological cells are well known in the art (see, Sambrook et al., Molecular Cloning: A Laboratory Manual, Cold Spring Harbor Laboratory, Cold Spring Harbor, N.Y., 1989; Ausubel et al., eds. Current Protocols in Molecular Biology, Wiley Interscience, N.Y., 1991; Bauer et al., J. Biol. Chem. 271: 23749–23755, 1996).

Making Membranes:

After phenotypic expression of the transformation, the mutant library is deposited on 47 mm diameter membranes, and the cells on the membranes are grown on agar plates until microcolonies (.about. 100 micron diameter) appear. A Nalgene 150 ml Analytical Filter Unit (130-4020 from Nalge Nunc International, Rochester, N.Y.) was used for deposition. After taking the unit apart and removing the 0.2 micron pore size membrane, 1–2 ml of LB media (Difco) is pipetted onto the remaining cellulosic support pad of the unit. In addition, 5–6 ml of LB media is pipetted into a sterile test tube (such as a Falcon 2059 tube). A 47 mm polyester 0.2 micron-pore size track-etch membrane (Osmonics Inc., Minnetonka, Minn.) is applied to the wetted cellulosic support pad and the filter unit is reassembled. Less than 200 microliters of the transformation, and ideally 50 microliters or less, is added to the LB media in the sterile test tube and gently vortexed to mix. This mixture is then poured into the filter unit. The filter unit is attached to a vacuum pump to deposit the cells on the polyester filter membrane. The unit is disassembled again and the polyester filter is transferred to an LBAC plate (LB agar (Difco) plates containing both 25 microgram/ml carbenicillin and 100 microgram/ml ampicillin). The time of the transfer is noted. The LBAC plate is preferably prewarmed at 37 degrees Celsius for about one hour before use. The same filter unit can be used for multiple membranes. The unit is routinely changed if there is concern about cross-contamination between membranes. If membranes with different dilutions of the same transformation are being prepared, the same filter unit is used but the membrane with the lowest colony density is prepared first, followed by the membrane with the next lowest colony density. The LBAC plates bearing the polyester membranes are incubated at 37 degrees Celsius overnight for 12–15 hours.

Induction plates are equilibrated overnight at 26 degrees Celsius, for example in a VWR low-temp incubator, model 2005 (South Plainfield, N.J.). Preferably, induction plates are only used if they are less than one week old. LB-agar induction medium contains 25 microgram/ml carbenicillin, 100 microgram/ml ampicillin and 0.2% inducer+0.5 mM $CuSO_4$. The inducer used in this example is arabinose.

Day 2:

Induction

After overnight incubation of the polyester membranes on LBAC plates, the membranes are examined for the appearance of microcolonies (.about. 100 micron diameter). After microcolonies have appeared on the membranes, the membranes are transferred to the induction plates that have been equilibrating overnight at 26 degrees Celsius, and the membranes are then returned to incubate at 26 degrees Celsius for at least four hours. The time at which they are transferred to the induction plates is noted.

To minimize differences in induction time, induction of membranes can be staggered in time. The number of membranes to be induced at the same time will depend on the amount of time each membrane requires to be analyzed (for example, three plates can be induced at the same time and subsequent batches of three plates can be induced hourly if each plate requires about 20 minutes to be assayed.) Plates that are not induced initially continue to grow at 37 degrees Celsius, but preferably do not grow longer than about 15 hours to minimize the size of the microcolonies.

Preparing assay plates

Assay plates are preferably made the same day that they will be used. This prevents the plates from drying out and minimizes the loss of peroxidase activity in the plate. When plates are not made on the same day that they are used, they are parafilmed and stored at 4 degrees Celsius.

Assay plates contain one percent agarose (BioRad), potassium phosphate buffer (approximately pH 7), cupric sulfate, 4CN, soybean peroxidase, and substrate. Both methyl-galactose and guar have been used as substrates. Stock solutions of methyl-galactose (1.2 M) and cupric sulfate (100 mM) are prepared with water. Stock solutions of 4CN (typically 200 mM) are prepared with dimethylformamide (DMF) as solvent. A 1% agarose solution is prepared by adding one gram agarose to each 100 ml of 50 mM potassium phosphate buffer and heating the mixture in a microwave oven (with swirling) until the agarose dissolves. If the agarose solidifies, it is reliquefied in a microwave oven. A 2% solution is made in a similar way. Assay plates can also be made with phosphate buffer of a different pH or with a different buffer solution, if GO activity under different buffer or pH conditions is desired.

Assay plates containing 5 mM methyl-galactose have been used to identify GO mutants with superior enzymatic activity relative to wild-type. These plates can be prepared as follows: Fifty ml conical tubes (such as Falcon 2070 tubes) and the petri dishes which will serve as assay plates are prewarmed to 70 degrees Celsius. The methyl-galactose stock solution, the 4CN stock solution and soybean peroxidase stock solution are prewarmed to room temperature. The buffered 1% agarose is liquefied and kept at a temperature of at least 42 degrees Celsius but preferably 10 to 20 degrees higher. A 40-ml assay mixture with 5 mM methyl-galactose is prepared by adding these components to a prewarmed 50 ml conical tube in the following order:

39.1 ml of 1% agarose in 50 mM potassium phosphate buffer (pH 7)

168 microliters of 1.2 M methyl-galactose 200 microliters of 100 mM cupric sulfate 300 microliters of 200 mM 4CN The mixture is briefly vortexed at this point. When the mixture has cooled to approximately 42 degrees Celsius, 200 microliters of soybean peroxidase (480 units/ml) are added to the mixture. The solution is vortexed again, and 8–10 ml of this mixture is pipetted into the prewarmed petri dishes. The resulting assay plates are allowed to cool at room temperature for 10–15 minutes before covering each dish.

Assay plates containing guar as substrate have also been prepared. The viscosity of guar solutions presents challenges for preparing assay plates. Two methods for preparing guar assay plates are described here. In the first method, the peroxidase is added to the assay solution before pouring the assay plate. In the second method, the peroxidase is spread on the surface of an assay plate after pouring an assay solution without peroxidase into a petri dish. The second method permits the preparer to pour a hotter (and thus less viscous) guar solution into the petri dish, since concerns about killing the peroxidase activity are obviated if the peroxidase is not in the assay mix.

In the first method, a 100 ml solution of 1.2% guar in 50 mM potassium phosphate buffer (pH 7) is prepared with stirring overnight at room temperature. The guar solution is made less viscous and more consistent by passing 50 ml of the guar solution back and forth between two 60 ml syringes connected by a micro-emulsifying needle (Popper & Sons, New Hyde Park, N.Y.). Thirty ml of the guar solution is transferred to a prewarmed 50 ml conical tube, and 0.3 g of agarose is added to the guar solution. The tube is heated in a microwave oven and shaken/vortexed until the agarose dissolved. Next, 450 microliters of 100 mM 4CN is added to the guar/agarose solution and mixed. Occasional microwaving is used to keep this solution (solution A) liquefied. Brief centrifugation in a table-top swinging bucket centrifuge reduces -the number of bubbles in the solution. The metal buckets are prewarmed at 70 degrees Celsius to minimize cooling of solution A. Ten ml of warm solution A is poured into a prewarmed 10 ml syringe attached to second ten ml syringe with a micro-emulsifying needle. Fifty microliters of 100 mM cupric sulfate is added, and the material is passed back and forth through the needle to mix. 75 microliters of soybean peroxidase is added and mixed in the same way. The resulting material is pushed out of the syringe into a petri dish, and the assay plate is allowed to harden, resulting in an assay plate containing approximately 1.2% guar.

The second method creates an assay plate that is smoother and has fewer bubbles. For this protocol, fifty microliters of 100 mM cupric sulfate is added to 10 ml of hot solution A in a 50 ml conical tube and the material is mixed/vortexed in the tube. Brief centrifugation (in pre-warmed swinging buckets) is used to remove bubbles. The resulting material is poured into a petri dish spinning on a spreading wheel. After the plate has solidified, 75 microliters of soybean peroxidase is pipetted on the surface, and glass beads are used to spread the enzyme evenly across the surface. The plate is wrapped with parafilm and allowed to equilibrate at 4 degrees Celsius overnight before use. This process results in an assay plate containing approximately 1.2% guar.

In another embodiment of this second method, the guar solution (after being passed back and forth through the micro-emulsifying needle) is mixed with an agarose solution, instead of powdered agarose. Both the guar solution and the agarose solution are used when hot (greater than 60 degrees Celsius). The following components are placed in a 60-ml syringe connected to a second syringe by a micro-emulsifying needle.

A 40 ml assay solution is comprised of:

20 ml of 1.2% guar (in 50 mM potassium phosphate buffer, pH 7)

20 ml of 2% agarose (in 50 mM potassium phosphate buffer, pH 7)

300 microliters of 200 mM 4CN 200 microliters of 100 mM cupric sulfate

The syringe assembly is prewarmed to 70 degrees Celsius before use. The hot solution is passed back and forth through the micro-emulsifying needle to thoroughly mix the solution. The entire solution is moved into one of the syringes, removed from the micro-emulsifying needle, and capped. The capped syringe is then briefly centrifuged in prewarmed swinging buckets to minimize the number of bubbles in the solution. The resulting solution is pushed out of the syringe into three petri dishes, while they are spinning on a spreading wheel. After the plate has solidified, 50–75 microliters of soybean peroxidase are pipetted on the surface and glass beads are used to spread the enzyme evenly across the surface. The plate is wrapped with parafilm and allowed to equilibrate at 4 degrees Celsius overnight before use. This process results in an assay plate containing approximately 0.6% guar.

Preparing the Kcat Instrument

The Kcat instrument is prepared for a kinetics run by setting software and hardware parameters so that they are suitable for a given calorimetric indicator. The instrument is set to 550 nm in absorption mode for monitoring 4CN conversion. The Kcat instrument is turned on about 30–60 minutes prior to use to allow the temperature-controlled reaction chamber to fully equilibrate to the desired temperature. Measurements for GO mutant libraries were made at 37 degrees Celsius. An assay plate is placed in the Kcat instrument so that it will also equilibrate to the desired temperature. An image of the assay plate is acquired to determine the desired exposure time and camera parameters. The exposure time is selected so that gray values of 40,000 to 50,000 (out of a possible 64,000) are obtained from the assay plate image. Typically, the camera is set for a 4-second exposure and the pixels are binned 2 by 2. Other parameter settings include the length of the kinetic run and the time interval between images. For kinetic runs of 15 minutes or less, images are typically acquired every 30 seconds. For kinetic runs greater than 15 minutes (and up to 60 minutes), images are typically acquired every 60 seconds.

Lysis

After induction of the microcolonies, the membrane covered with microcolonies is exposed to chloroform vapor to lyse or permeabilize the cells in the microcolonies. The top part of a Nalgene 150 ml Analytical Filter Unit (130-4020 from Nalge Nunc International, Rochester, N.Y.) is used to create a lysis chamber. After taking the unit apart, the cellulosic support pad is removed from the lower half of the unit and placed in the top half of the unit (covering the opening at the bottom). This lysis chamber is placed over the membrane while it is still on the surface of the induction plate. In a smooth outwardly spiraling motion, about 1 ml of chloroform is pipetted onto the cellulosic support pad in the lysis chamber. The apparatus is covered with a petri dish lid and allowed to incubate for 45–60 seconds. The lysis chamber is then removed and the membrane is transferred to an assay plate that has been prewarmed in the Kcat instrument. The membrane is placed on the assay plate so that as much of the membrane as possible is within the field of view of the camera.

Kcat Instrument Operation for the GO Assay

Once the membrane containing the lysed microcolonies is placed on the assay plate in the Kcat instrument, the door to the reaction chamber is closed, and the kinetic run is started. The microcolonies are imaged automatically at set time intervals for the duration of the kinetic run. After image acquisition is completed, kinetic analysis of microcolonies that have been imaged at single-pixel resolution is performed. The data is radiometrically calibrated for optical density. In one type of analysis, flat field division by a "blank" image corrects for any inhomogeneous illumination in the images. Typically this "blank" image is the zero timepoint image. The darkest pixels (those with the lowest gray values) are selected, and the absorbance of each of the selected pixels at each timepoint is determined from the acquired images. A contour plot containing the absorbance versus time information for every selected pixel is generated from the data, and this data is sorted to identify the pixels with superior reaction kinetics. The desired pixels are then color-coded in an image of the microcolonies to indicate which of the microcolonies have the desired reaction kinetics.

Once microcolonies with superior reaction kinetics are identified on the membrane, a portion of the microcolony can be recovered with a pipette tip. This portion is transferred to a tube containing a buffered solution, and the DNA obtained is retransformed into *E. coli*. Membranes bearing small numbers of microcolonies (preferably less than 100) are produced using this transformation mixture and these are reassayed with the Kcat instrument. This repurification step is usually necessary because the high density of microcolonies on the original membrane often means that the DNA obtained during the recovery step contains DNA from multiple microcolonies. A well isolated microcolony with the desired kinetic properties is then recovered from this second membrane and is transferred to a tube containing a buffered solution. The DNA so obtained is retransformed into *E. coli*. Single colonies from this transformation are grown in LB media, glycerol stocks of the culture are made, DNA from the culture is isolated and analyzed, and lysates are analyzed as described below in the next section.

C. Characterization of GO Enzymes

Comparison of wildtype and variant GO enzymes comprises: i) growth and induction of the galactose oxidase enzyme in an *E. coli* host, ii) determination of the rate of oxidation of galactose versus several concentrations of methyl-α-D-galactose for each variant, and iii) fitting the resulting velocity versus concentration data to the Michaelis-Menten equation to determine the parameters Km and Vmax. Km, Vmax, and Vmax/Km are used to compare the variant enzymes to the wild type. The velocity of each reaction ($\Delta A_{405}$/min) was determined by a linear fit to the increase in absorbance for the first 2 minutes of reaction. The velocity versus concentration of methyl-α-D-galactose was then fit to the Michaelis-Menten equation (vel=(Vmax[S]/ (Km+[S]), where S=methyl-α-D-galactose) to determine Km and Vmax.

From a frozen culture of *E. coli* (XL1 blue or DH10B) containing the galactose oxidase gene on an expression plasmid, single colonies were obtained by streaking the culture onto a sterile petri plate containing LB/agar with 60 µg/mL of carbenicillin (LB/carb) and growing over night at 37° C. A single colony was used to inoculate 3.0 mL of LB media containing 60 µg/mL of carbenicillin, 0.002% of L-arabinose, and 0.32 mM $CuSO_4$. The culture was grown for 24 hours at 26° C. with shaking to yield a saturated culture. BPER lysis reagent (3.0 mL, Pierce Biochemical) was added to the culture, the mixture vortexed briefly, allowed to stand at RT for 15 min, then centrifuged at 3,500 rpm for 30 min to pellet the insoluble cell debris. The lysate was used in the assays without further purification and can be stored at 4° C.

All components except the lysate were dissolved in buffer containing 50 mM potassium phosphate, 1 mM $CuSO_4$, pH 7.0. The 250 µL assay mixture contained 1 mM ABTS (2,2'-azino-bis(3-ethylbenzthiazoline-6-sulfonic acid, Sigma Chemical Co.), 1 U/mL Horse Radish Peroxidase (HRP, Sigma Chemical Co.), a variable amount of methyl-α-D-galactose (Sigma Chemical Co.), and 1.0 µL of the culture lysate. The concentrations of methyl-α-D-galactose varied from 0.72 mM to 200 mM.

Alternatively, partially hydrolyzed guar is used as the substrate, prepared as follows: A 1% aqueous solution of cationic guar containing 1 M HCl is heated at 50° C. for 5 hours, followed by neutralization with sodium hydroxide, filtration through a 30,000 mwt filter membrane and lyophilization. The resulting cake is dissolved in buffer containing 50 mM potassium phosphate, 1 mM $CuSO_4$, pH 7.0 and mixed slowly over 12 h to insure dissolution.

An assay is then performed similarly to that for the methyl galactose: All components except the lysate (containing GO or vGO enzymes) are dissolved in buffer containing 50 mM potassium phosphate, 1 mM $CuSO_4$, pH 7.0. The 240 µL assay mixture contained 1 mM ABTS (2,2'-azino-bis(3-ethylbenzthiazoline-6-sulfonic acid, Sigma Chemical Co.), 1 U/mL Horse Radish Peroxidase (HRP, Sigma Chemical Co.), 1% partially hydrolyzed cationic guar and 10 µL of the culture lysate. The oxidase activity (as measured by production of peroxide and coupled oxidation of ABTS via HRP) is monitored by the increase in absorbance at 405 nm due to the formation of oxidized ABTS in a uv/vis plate reader for at least 10 minutes. Reactions were run in duplicate.

Methyl-α-D-galactose is an excellent proxy for guar, in that GO enzymes which oxidize the former also are active on the latter. We measured and compared the relative activities of mutants both on guar and on methyl-galactose. The activity of cell lysates on 1% solutions of low molecular weight guar produced by acid hydrolysis and ultrafiltration was measured. This guar has significant but reduced viscosity, permitting reproducible liquid phase measurements on a limited number of samples. Size-exclusion chromatography and HPLC showed that the resulting hydrolyzed guar had a narrow distribution of molecular weights and that cleavage did not preferentially release galactose side-chains (Dr. Lei Qiao, personal communication.) The activity ($\Delta$OD 405/min) of each mutant in 1% hydrolyzed guar was determined in liquid phase and wildtype-relative rates were calculated.

Vmax and Km were measured for several mutants using methyl-galactose as a substrate in the liquid phase assay. This assay is similar to the solid phase assay used to screen mutants, but uses ABTS as a chromogenic substrate instead of 4CN. Vmax/Km values were then used to calculate wildtype-relative activity towards methyl-galactose. Table 4 shows the correlation between the relative activity of mutants on guar vs. methyl-galactose.

TABLE 4

| Clone | Km (mM) | Vmax ($\Delta$OD$_{405}$/ min) | Vmax/Km (me-gal) | Vmax/Km Relative to WT, on methyl galactose | Activity ($\Delta$OD$_{405}$/ min) Relative to WT, on guar |
|---|---|---|---|---|---|
| K3 (WT) | 32.2 | 0.12 | 0.003665 | 1.0 | 1 |
| GO.1-4 | 30.3 | 0.27 | 0.009002 | 2.5 | 1.8 |
| GO.05-1 | 31.7 | 0.32 | 0.010127 | 2.8 | 2.2 |
| 8.2.2 | 11.6 | 0.18 | 0.015278 | 4.2 | 2.8 |
| 2-1 | 10.2 | 0.23 | 0.022549 | 6.2 | 4.3 |
| 7.3.2 | 11.7 | 0.32 | 0.027781 | 7.6 | 11.3 |
| GO.1-10 | 11.1 | 0.32 | 0.028634 | 7.8 | 2.7 |
| 6-1 | 9.7 | 0.39 | 0.040086 | 10.9 | 2.5 |
| 7.1.1 | 12.3 | 0.51 | 0.041095 | 11.2 | 8.5 |
| 7.3.1 | 11.7 | 0.53 | 0.045466 | 12.4 | 9.4 |
| 7.5.1 | 10.3 | 0.47 | 0.046215 | 12.6 | 8.9 |
| A3R | 9.0 | 0.47 | 0.052393 | 14.3 | 7.8 |
| 7.5.2 | 9.2 | 0.51 | 0.055315 | 15.1 | 10.9 |
| 8-1 | 10.5 | 0.61 | 0.057864 | 15.8 | 8.6 |

As shown in Table 4, high activity towards methyl-galactose correlates well with high-activity towards guar. Most importantly, mutants that were identified as being superior using methyl-galactose as substrate are also superior using guar as the substrate. Additionally, one variant, 7.3.2, showed superior activity on guar relative to methyl galactose, demonstrating improved activity on a substrate other than methyl galactose.

D. Directed Evolution: Mutagenesis Via Error Prone PCR

Many methods of mutagenesis are useful for generating mutants, however, error prone PCR (EPP) was chosen for its suitability to generating large numbers of mutants in a brief period of time.

Error-prone PCR was performed according to previously published methods (e.g., Leung et al., 1989, Technique 1:11–15). PCR products were cloned using Xho I and Hind III sites to make mutant libraries, except for the libraries generated using clones GO. 1-3 or 8-1 as templates which were cloned using a Pst I site internal to the GO orf and Hind III.

EPP encompassing most (~2 kb) of the GO orf was performed to yield two libraries in which approximately 58% and 79% of mutants, respectively were inactive. The latter library had a mutation rate of about 0.3% (6 mutations detected in 2184 bp of sequence from randomly picked clones). Mutants were screened using the above-described high throughput screening method for improved activity at 37° C. relative to the wildtype clones present as a background on each assay plate. Two mutants were picked from the assay plate: mutants GO. 1-7 and GO. 1-8 (see Table 5). Twenty one more plates were assayed to give a total of 7 mutants demonstrating improved enzymatic activity. Each mutant, once purified, was compared with wildtype using Kcat to ensure that it was indeed more active.

Characterization of Improved Mutants

As can be seen in Table 5, three types of variants expressed by these mutants (C383S, Y436N/H and V494A) could be clearly assigned to the increased activity of the mutants. Two of these (C383S and Y436N/H) recurred in several mutants, and all three occurred alone in at least one clone.

TABLE 5

| Origin | Clone Name | Relevant Amino Acid Substitutions | Other Amino Acid Substitutions | Km (mM) | Vmax ($\Delta$OD$_{405}$/ min) | Vmax/Km ($\Delta$OD$_{405}$/ min mM × 1000) | Vmax/Km rel. to wild type |
|---|---|---|---|---|---|---|---|
| Wildtype | K3 | | | 32.2 | 0.12 | 3.7 | 1 |
| EPP on wildtype | GO.1-3 | Y436N | | ~30 | 0.43 | 14.3 | 3.9 |
| | GO.1-4 | V494A | | 30.3 | 0.27 | 9 | 2.5 |
| | GO.1-7 | C383S | D258E, N314Y | ~13 | ~0.2 | ~15 | ~4.1 |
| | GO.1-8 | Y436N | | ~30 | ~0.3 | 10 | ~2.7 |
| | GO.1-10 | C383S | | 11.1 | 0.32 | 28.63 | 7.8 |
| | GO.1-13 | C383S | N46D | ~14 | ~0.3 | 21 | 5.7 |
| | GO.05-1 | Y436H | | 31.7 | 0.32 | 10.1 | 2.8 |
| Manual Recomb. | 2-1 | C383S | | 10.2 | 0.23 | 22.55 | 6.2 |
| | 4-1 | | N46D | ~30 | ~0.1 | ~3 | ~0.8 |
| | 6-1 | C383S, Y436H | N46D | 9.7 | 0.39 | 40.09 | 10.9 |
| | 8-1 | C383S, Y436H, V494A | | 10.5 | 0.61 | 57.86 | 15.8 |
| EPP on GO.1-3 | A1R | Q63K, Y436N | G558N | 31.5 | 0.4 | 12.85 | 3.5 |
| | A2R | Q63K, Y436N | G558N | 29 | 0.37 | 12.83 | 3.5 |
| | A3R | Q63K, C383S, Y436N | | 9 | 0.47 | 52.39 | 14.3 |
| | A4R | Q63K, C383S, Y436N, V494A | S373F | 9.7 | 0.54 | 55.13 | 15.0 |
| | A6R | Q63K, C383S, Y436N | | 33.7 | 0.38 | 11.26 | 3.1 |
| | A8R | Q63K, C383S, Y436N | | 9.7 | 0.43 | 44.4 | 12.1 |
| | A9R | Q63K | | 35.1 | 0.19 | 5.29 | 1.4 |
| | A11R | Y436N | | 25 | 0.36 | 14.53 | 4.0 |

TABLE 5-continued

| Origin | Clone Name | Relevant Amino Acid Substitutions | Other Amino Acid Substitutions | Km (mM) | Vmax ($\Delta OD_{405}$/min) | Vmax/Km ($\Delta OD_{405}$/min mM × 1000) | Vmax/Km rel. to wild type |
|---|---|---|---|---|---|---|---|
| EPP on 8-1 | 7.1.1 | C383S, Y436H | A315G, Y358H | 12.3 | 0.51 | 41.09 | 11.2 |
| | 7.3.1 | C383S, Y436H, V494A | V365E | 11.7 | 0.53 | 45.47 | 12.4 |
| | 7.3.2 | C383S, Y436H, V494A | K248E, T352S, K366R | 11.7 | 0.32 | 27.78 | 7.6 |
| | 7.5.1 | Y436H, V494A | N318D, V477D, A626S | 10.3 | 0.47 | 46.21 | 12.6 |
| | 7.5.2 | C383S, Y436H, V494A | V268E, M278V, S306T, G376S, R636H | 9.2 | 0.51 | 55.31 | 15.1 |
| | 8.2.1 | C383S, Y436H, V494A | D216E, Q267L | 12.3 | 0.23 | 18.83 | 5.1 |
| | 8.2.2 | C383S, Y436H, V494A, Q63K | V241I, K249V, I417V | 11.6 | 0.18 | 15.28 | 4.2 |

Based on the expectation that mutations can be added to the same clone to yield a variant that is several fold better than wildtype, the three mutations discussed above were manually recombined (MR) into a double mutant, named 6-1 (having C383S, Y436H); the presence of the additional substitution N46D does not confer superior activity, as demonstrated by a clone having only that substitution. Manual recombination was also employed to produce a triple mutant, named 8-1 (having the substitutions C383S, Y436H, and V494A). The latter shows an approximately 16-fold higher activity than wildtype towards methyl-galactose, as measured by the ratio of Vmax to Km.

The observation that only three useful mutations were obtained in a first round of screening suggested that most of the single mutants that could be made by EPP had been sampled. To investigate whether performing EPP on one of the improved mutants would cause one or both of the other two mutations to simply be added to the first, and in an effort to generate variants with further improvements in the enzyme's activity, EPP was performed on the triple mutant (8-1) and on GO.1-3 (Y436N).

Table 5 shows that only one new mutation (Q63K) was found that produces a mild increase in activity. All other improvements in activity were due to the same mutations found in the first round of EPP. Theoretically, approximately 6000 different point mutants can be found in a library spanning the entire GO orf. By screening large numbers of mutants, it is likely that all the single mutants that EPP can generate had been sampled. Interestingly, one mutant (A4R) bore all three of the mutations identified previously, which is a rare find given the large number of possible double-mutants in this library (~8.9×10$^6$).

The site of the substitution yielding an improved variant apparently need not be located in or near the active site of the enzyme. For example, C383S and V494A are near the active site while the others are not. C383S may improve stability to $H_2O_2$ due to loss of a reactive sulfhydryl group.

Directed evolution is generally successful in producing mutant enzymes with improved thermostability or resistance to denaturation in organic solvents. Cunningham et al., (1987), Protein Eng 1, 319–25; Chen et al., (1993), Proc Natl Acad Sci U S A 90, 5618–22; Chen et al., (1991), Biotechnology (N Y) 9, 1073–7.

Key to this success is the simplicity of the process. First, error-prone PCR is used to generate thousands of mutants that are then screened for improved activity under certain conditions. Second, the most active mutant observed in the screen is used in a new round of error-prone PCR to produce a second generation of mutants that is again screened for improved activity. By maintaining low rates of mutagenesis (~1 amino acid substitution per gene) one ensures that most of the 3000 single mutants that can be generated in a 1000 bp gene are sampled by the screening method. Therefore, if there exists an amino acid substitution that can be achieved by a single mutation and that can improve some property of an enzyme, a fairly modest screening effort will produce it.

Two clones, GOK3 (wildtype) and 8-1 described above and in Table 5, were subjected to further mutation by EPP to generate mutant libraries from which mutants exhibiting improved thermostability were isolated. The two mutant libraries were screened using the Kcat instrument to identify mutants with increased thermostability. The screen involved the following steps: 1) grow, induce, and lyse microcolonies expressing enzyme variants on a porous membrane as described above; 2) transfer the membrane to a petri dish containing a piece of Whatman 114 filter paper imbibed with 50 mM potassium phosphate buffer pH 7, said petri dish and buffer having been pre-incubated at 64–70° C. (depending on the experiment) by floating in a circulating water bath for 5 minutes. Prior to floating in the circulating water bath, the petri dish and the buffer solution are pre-warmed at 70° C. in an incubator/oven; 3) incubate the membrane, now on the surface of the filter in the petri dish, at 64–70° C. (again depending on the experiment) for 8–10 minutes; 4) transfer the membrane to a petri dish containing a piece of Whatman 114 filter paper imbibed with 50 mM potassium phosphate buffer pH 7, said petri dish and buffer having been pre-incubated at 37 degrees Celsius; and 5) transfer the membrane to an assay plate prewarmed to 37 degrees Celsius in the Kcat instrument and start a kinetic run. Several mutants showing greater post-heat treatment activity than their parent (either GOK3 or 8-1) were picked for further characterization. The enzyme variants expressed by the resulting mutant clones were incubated for 10 minutes at a range of different temperatures, then brought back to room temperature and tested for enzymatic activity. Three clones from the mutant libraries that were generated from clone GOK3 were found to have improved thermostability; these were named GO.05-1h1B, GO.05-1h1C and GO.1h1C. Four clones from the mutant libraries that were generated from clone 8-1 were found to have improved thermostability; these were named G08-1h1A, G08-1h2A, G08-1h3A, and G08-1h4A.

Table 6 below shows the results for these variant GO enzymes, including the wildtype GOK3 and the original 8-1 enzymes. The data show that GOK3 has lost about 72% of its activity after a 60° C. incubation while mutant clones derived from it have lost no more than 30% of their initial activity. Also, 8-1 appears less thermostable than GOK3. Mutants derived from this clone, however, show thermostability comparable to GOK3. Thus, mutations enhancing thermostability have restored wildtype-like thermnostability to 8-1.

TABLE 6

| Clone | Normalized activity remaining after incubation at temperature* | | | | |
|---|---|---|---|---|---|
| | 50 C. | 55 C. | 60 C. | 65 C. | 70 C. |
| GOK3 | 1.00 | 0.69 | 0.28 | 0.21 | 0.11 |
| GO.05h1B | 1.00 | 1.12 | 0.70 | 0.23 | 0.23 |
| GO.05h1C | 1.00 | 0.93 | 0.90 | 0.39 | 0.37 |
| GO.1h1C | 1.00 | 0.92 | 0.88 | 0.85 | 0.33 |
| 8-1 | 1.00 | 0.37 | 0.04 | 0.01 | 0.01 |
| GO8-1h1A | 1.00 | 0.84 | 0.22 | 0.01 | 0.01 |
| GO8-1h2A | 1.00 | 0.84 | 0.35 | 0.02 | 0.01 |
| GO8-1h3A | 1.00 | 0.83 | 0.31 | 0.00 | 0.00 |
| GO8-1h4A | 1.00 | 0.79 | 0.31 | 0.12 | 0.11 |

*All mutants normalized to their respective activity at 50° C.

Relative to the wildtype enzyme, the improved thermostability enzymes had the amino acid substitutions shown below in Table 7.

TABLE 7

| GO enzyme | Amino Acid Substitutions |
|---|---|
| GO.05h1B | N115H |
| GO.05h1C | G195E, S553C |
| GO.1h1C | G6R |
| GO8-1h1A | Q238L, K342E, C383S, Y436H, V494A |
| GO8-1h2A | N427T, Y436H, V494A |
| GO8-1h3A | Q63K, G195A, C383S, Y436H, V494A |
| GO8-1h4A | Q63K |

As can be seen from the list of substitutions in the 8-1 derivatives, clone G08-1H2A had a reversion of the C383S substitution to the wildtype sequence. This suggests that the C383S substitution may decrease thernostability and is consistent with the observation that 8-1 is less thermostable than wildtype. Clone G08-1H4A is believed to be a contaminant and has wildtype-like (i.e., GOK3-like) thermostability.

The amino acid sequences of several of the preferred variant GO enzymes are found in Table 8 below, with the substitutions, relative to the wildtype, shown in bold. These sequences are illustrative examples, and it will be understood that the amino acid sequences for other variants of the invention will be readily discerned given the wildtype sequence (SEQ ID NO: 2) and the substitutions described with the given nomenclature.

TABLE 8

(Amino acid substitutions relative to wt are in bold; DNA mutations are not highlighted.)

The mature amino acid sequence for GO8-1, (SEQ ID NO: 3) is

ASAPIGSAISRNNWAVTCDSAQSGNECNKATDGNKDTFWHTFYGANGDPKPPHTYTIDMKTTQNVNGLSM

LPRQDGNQNGWIGRHEVYLSSDGTNWGSPVASGSWFADSTTKYSNFETRPARYVRLVAITEANGQPWTSI

AEINVFQASSYTAPQPGLGRWGPTIDLPIVPAAAAIEPTSGRVLMWSSYRNDAFGGSPGGITLTSSWDPS

TGIVSDRTVTVTKHDMFCPGISMDGNGQIVVTGGNDAKKTSLYDSSSDSWIPGPDMQVARGYQSSATMSD

GRVFTIGGSWSGGVFEKNGEVYSPSSKTWTSLPNAKVNPMLTADKQGLYRSDNHAWLFGWKKGSVFQAGP

STAMNWYYTSGSGDVKSAGKRQSNRGVAPDANSGNAVMYDAVKGKILTFGGSPDYQDSDATTNAHIITLG

EPGTSPNTVFASNGLHFARTFHTSVVLBDGSTFTTGGQRRGIPFEDSTPVFTPEIYVPEQDTFYKQNPNS

IVPAYHSTSLLLPDGRVFNGGGGLCGDCTTNHFDAQIFTPNYLYNSNGNLATRPKITRTSTQSVKVGGRI

TISTDSSISKASLIRYGTATHTVNTDQRRIPLTLTNNGGNSYSFQVPSDSGVALPGYWMLFVMNSAGVPS

VASTIRVTQ

The mature amino acid sequence of GO8-1H3A (SEQ ID NO: 4) is

ASAPIGSAISRNNWAVTCDSAWSGNECNKAI DGNKDTFWHTFYGANGDPKPPHTYTIDMKTTKNVNGLSMLPRQDGNQNG

WIGRHEVYLSSDGTNWGSPVASGSWFADSTTKYSNFETRPARYVRLVAITEANGQPWTSIAEINVFQASSYTAPQPGLGR

WGPTIDLPIVPAAAAIEPTSGRVLMWSSYRNDAFA GSPGGITLTSSWDPSTGIVSDRTVTVTKHDMFCPGISMDGNGQIV

VTGGNDAKKTSLYDSSSDSWIPGPDMQVARGYQSSATNSDGRVFTIGGSWSGGVFEKNGEVYSPSSKTWTSLPNAKVNPM

LTADKQGLYRSDNHWLFGWKKGSVFQAGPSTAMNWYYTSGSGDVBZSAGKRQSNRGVAPDAMSGNAVMYDAVKGKILTFG

GSPDYQDSDATTNABIITLGEPGTSPNTVFASNGLHFARTFHTSVVLPDGSTFLTGGQRRGIPFEDSTPVFTPEIYVPEQ

DTFYKQNPNSIVRAYHSISLLLPDGRVFNGGGGLCGDCTTNHFDAQIFTPNYLYNSNGNLATRPKITRTSTQSVKVGGRI

TABLE 8-continued (Amino acid substitutions relative to wt are in bold; DNA mutations are not highlighted.)

TISTDSSISKASLIRYGTATHTVNTDQRRIPLTLTNNGGNSYSFQVPSDSCVALPGYWMLFVMNSAGVPSVASTIRVTQ
The mature amino acid sequence of clone 7.3.2 (SEQ ID NO: 5) is

ASAPIGSAISRNNWAVTCDSAQSGNECNKAIDGNKDTFWHTFYGANGDPKPPHTYTIDMKTTQNVNGLSMLPRQDGNQNG

WIGRHEVYLSSDGTNWGSPVASGSWFADSTTKYSNFETRPARYVRLVAITEANCQPWTSIAEINVFQASSYTAPQPGLGR

WGPTIDLFIVPAAAAIEFTSGRVLMWSSYRNDAFGGSPGGITLTSSWDPSTGIVSDRTVTVTKHDMFCPGISMDGNGQIV

VTGGNDAZKTSLYDSSSDSWIPGPDMQVARCYQSSATMSDGRVFTIGGSWSGGVFEKNGEVYSFSSKTWTSLPNAKVNPM

LTADKQGLYRSDNHAWLFGWKKGSVFQAGPSSAMNWYYTSGSGDVRSAGKRQSNRGVAPDAMSGNAVMYDAVKGKILTFG

GSPDYQDSDATTNAHIITLGEPGTSPNTVFASNGLHFARTFHTSVVLPDGSTFITGGQRRGIFFEDSTFVFTFEIYVFEQ

DTFYKQNPNSIVPAYHSISLLLPDGRVFNCGCGLCGDCTTNHFDAQIFTPNYLYNSNGNLATRFKITRTSTQSVKVCGRI

TISTDSSISKASLIRYGTATHTVNTDQRRIPLTLTUNGGNSYSFQVPSDSGVALPGYWMLFVMNSAGVPSVASTIRVTQ
The DNA sequence for the entire orf of GO8-1H3A (SEQ ID NO: 6) is ATGAAACACCTTTTAACACTCGCTCTTTGCTTCTCGACCATCAATGCTGTTGCTGTCACCGTCCCTCACAAGGCCGTAGGAACTGG AATTCCTGAAGGGAGTCTTCAGTTCCTGAGCCTTCGAGCCTCAGCACCTATCGGAAGCGCCATTTCTCGCAACAACTGGGCCGTCA CTTGCGACAGTGCACAGTCGGGAAATGAATGCAACAAGGCCATTGATGGCAACAAGGATACCTTTTGGCACACATTCTATGGCGCC AACGGGGATCCAAAGCCCCCTCACACATACACGATTGACATGAAGACAACTAAGAACGTCAACGGCTTGTCTATGCTGCCTCGACA GGATGGTAACCAAAACGGCTGGATCGGTCGCCATGAGGTTTATCTAAGCTCAGATGGCACAAACTGGGGCAGCCCTGTTGCGTCAG GTAGTTGGTTCGCCGACTCTACTACAAAATACTCGAACTTTGAAACTCGCCCTGCTCGCTATGTTCGTCTTGTCGCTATCACTGAA GCGAATGGCCAGCCTTGGACTAGCATTGCAGAGATCAACGTCTTCCAAGCTAGTTCTTACACAGGCCCCCAGCCTGGTCTTGGACG CTGGGGTCCGACTATTGACTTACCGATTGTTCCTGCGGCTGCAGCAATTGAACCGACATCGGGACGAGTCCTTATGTGGTCTTCAT ATCGCAATGATGCATTTGCAGGATCCCCTGGTGGTATCACTTTGACGTCTTCCTGGGATCCATCCACTGGTATTGTTTCCGACCGC ACTGTGACAGTCACCAAGCATGATATGTTCTGCCCTGGTATCTCCATGGATGGTAACGGTCAGATCGTAGTCACAGGTGGCAACGA TGCCAAGAAGACCAGTTTGTATGATTCATCTAGCGATAGCTGGATCCCGGGACCTGACATCCAAGTGGCTCGTGGGTATCAGTCAT CAGCTACCATGTCAGACGGTCGTGTTTTTACCATTGGAGGCTCCTGGAGCGGTGGCGTATTTGAGAAGAATGGCGAAGTCTATAGC CCATGTTCAAAGACATGGACGTCCCTACCCAATGCCAAGGTCAACCCAATGTTGACGGCTGACAAGCAAGGATTGTACCGTTCAGA CAACCACGCGTGGCTCTTTGGATGAAGAAGGGTTCGGTGTTCCAAGCGGGACCTAGCACAGCCATGAACTGGTACTATACCAGTG GAAGTCGTGATCTGAAGTCAGCCGGAAAACGCCAGTCTAACCGTGGTCTAGCCCCTGATGCCATGAGCGGAAACGCTGTCATGTAC GACGCCGTTAAAGGAAAGATCCTGACCTTTGGCGGCTCCCCAGATTATCAAGACTCTGACGCCACAACCAACGCCCACATCATCAC CCTCGGTGAACCCGGTACCTCTCCCAACACTGTCTTTGCTAGCAATGGGTTCCACTTTCCCCGAACGTTTCACACTTCTGTTGTTC TTCCAGACGGAAGCACGTTTATTACAGGAGGCCAACGACGTGGAATTCCGTTCGAGGATTCAACCCCGGTATTTACACCTGAGATC TACGTCCCTGAACAAGACACTTTCTACAAGCAGAACCCCAACTCCATTGTTCGCGCCTACCATAGCATTTCCCTTTTGTTACCTGA TGGCAGGGTATTTAACGGTGGTGGTGGTCTTTGTGGCGATTGTACGACGAATCATTTCGACGCGCAAATCTTTACGCCAAACTATC TTTACAATAGGAACGGCAACCTCGCGACACGTCCCAGATTACCCAGAACCTCTACACACAGCGTCAACGTCGGTGGCAGAATTACA ATCTCGACGGATTCTTCGATTAGCAAGGCGTCCTTGATTCGCTATGGTACAGCGACACACGGTTAATACTGACCAGCGCCGCAT TCCCCTGACTCTGACAAACAATGGAGGAAATAGCTATTCCTTCCAAGTTCCTACCGACTCTGCTGTTGCTTTGCCTGGCTACTGGA TGTTGTTCGTGATGAACTCGGCCGGTGTTCCTAGTGTGGCTTCGACGATTCGCGTTACTCAGTGATAA
The DNA sequence for the entire orf of 7.3.2 (SEQ ID NO: 7) is

ATGAAACACCTTTTAACACTCGCTCTTTGCTTCTCGAGCATCAATGCTGTTGCTGTCACCGTCCCTCACAAGGCCGTA

GGAACTGGAATTCCTGAAGGGAGTCTTCAGTTCCTGAGCCTTCGAGCCTCAGCACCTATCGGAAGCGCCATTTCTCGC

AACAACTGGGCCGTCACTTGCGACAGTGCACAGTCGGGAAATGAATGCAACAAGGCCATTGATGGCAACAAGGATACC

TABLE 8-continued (Amino acid substitutions relative to wt are in bold; DNA mutations are not highlighted.)

TTTTGGCACACATTCTATGGCGCCAACGGGGATCCAAAGCCCCCTCACACATACACGATTGACATGAAGACAACTCAG

AACGTCAACGCCTTGTCTATGCTGCCTCGACAGGATGGTAACCAAAACGGCTGGATCGGTCGCCATGAGGTTTATCTA

AGCTCAGATGGCACAAACTGGGGCAGCCCTGTTGCGTCAGGTAGTTGGTTCGCCGACTCTACTACAAAATACTCCAAC

TTTGAAACTCGCCCTGCTCGCTATGTTCGTCTTGTCGCTATCACTGAAGCGAATGGCCAGCCTTGGACTAGCATTCCA

GAGATCAACGTCTTCCAAGCTAGTTCTTACACAGCCCCCCAGCCTGGTCTTGGACGCTGGGGTCCGACTATTGACTTA

CCGATTGTTCCTGCGGCTGCAGGGATTGAACCGACATCGGGACGAGTCCTTATGTGGTCTTCATATCGCAATGATCCA

TTTGGAGGATCCCCTGGTGGTATCACTTTGACGTCTTCCTGGGATCCATCCACTGGTATTGTTTCCGACCGCACTGTG

ACAGTCACCAAGCATGATATGTTCTGCCCTGGTATCTCCATGGATGGTAACGGTCAGATCGTAGTCACAGGTGGCAAC

GATGCCGAGAAGACCAGTTTGTATGATTCATCTAGCGATAGCTGGATCCCGGGACCTGACATGCAAGTGGCTCGTGGG

TATCAGTCATCAGCTACCATGTCAGACGGTCGTGTTTTTACCATTGGAGGCTCCTGGAGCGGTGGCGTATTTGAGAAG

AATCGCGAAGTCTATAGCCCATCTTCAAAGACATG3ACGTCCCTACCCAATGCCAAGGTCAACCCAATCTTGACGGCT

GACAAGCAAGGATTGTACCGTTCAGACAACCACGCGTGGCTCTTTGGATGGAAGAAGGGTTCGGTGTTCCAAGCGGGA

CCTAGCTCAGCCATGAACTGGTACTATACCAGTGGAAGTGGTGATGTGAGGTCAGCCGGAAAACGCCAGTCTAACCGT

GGTGTAGCCCCTGATGCCATGAGCGGAAACGCTGTCATGTACGACGCCGTTAAAGGAAAGATCCTGACCTTTGGCGGC

TCCCCAGATTATCAAGACTCTGACGCCACAACCAACGCCCACATCATCACCCTCGGTGAACCCGGTACCTCTCCCAAC

ACTGTCTTTGCTAGCAATGGGTTGCACTTTGCCCGAACGTTTCACACCTCTGTTGTTCTTCCAGACGGAAGCACGTTT

ATTACAGGAGGCCAACGACGTGGAATTCCGTTCGAGGATTCAACCCCGGTATTTACACCTGAGATCTACGTCCCTGAA

CAAGACACTTTCTACAAGCAGAACCCCAACTCCATTGTTCGCGCCTACCATAGCATTTCCCTTTTGTTACCTGATGGC

AGGGTATTTAACGGTGGTGGTGGTCTTTGTGGCGATTGTACCACGAATCATTTCGACGCGCAAATCTTTACGCCAAAC

TATCTTTACAATAGCAACGGCAACCTCGCGACACGTCCCAGATTACCAGAACCTCTACACAGAGCGTGCAAGGTCGGT

GGCAGAATTACAATCTCGACGGATTCTTCGATTAGCAAGCGTCGTTGATTCGCTATGGTACAGCGACACACACGGTT

AATACTGACCAGCGCCGCATTCCCCTGACTCTGACAAACAATGGAGGAAATAGCTATTCTTTCCAAGTTCCTAGCCAC

TCTGGTGTTGCTTTGCCTGGCTAGTGGATGTTGTTCGTGATGAACTCGGCCGGTGTTCCTAGTGTGGCTTCGACGATT

CGCGTTACTCAGTGATAA□

The DNA sequence for the entire orf of GO8-1 (SEQ ID NO: 8) is

ATGAAACACCTTTTAACACTCGCTCTTTGCTTCTCGAGCATCAATGCTGTTGCTGTCACCGTCCCTCACAAGGCCGTA

GGAACTGGAATTCCTGAAGGGAGTCTTCAGTTCCTGAGCCTTCGAGCCTCAGCACCTATCGGAAGCGCCATTTCTCGC

AACAACTGGGCCGTCACTTGCGACAGTGCACAGTCGGGAAATGAATGCAACAAGGCCATTGATGGCAACAAGGATACC

TTTTGGCACACATTCTATGGCGCCAACGGGGATCCAAAGCCCCCTCACACATACACGATTGACATGAAGACAACTCAG

AACGTCAACGGCTTGTCTATGCTGCCTCGACAGGATGGTAACCAAAACGGCTGGATCGGTCGCCATGAGGTTTATCTA

AGCTCAGATGGCACAAACTGGGGCAGCCCTGTTGCGTCAGGTAGTTCGTTCGCCGACTCTACTACAAAATACTCCAAC

TTTGAAACTCCCCCTGCTCGCTATGTTCGTCTTGTCGCTATCACTGAAGCGAATGGCCAGCCTTGGACTAGCATTGCA

GAGATCAACGTCTTCCAAGCTAGTTCTTACACAGCCCCCCAGCCTGGTCTTGGACGCTGGGGTCCGACTATTGACTTA

CCGATTGTTCCTGCCGCTGCAGCATTGAAACCGACATCGGGACGAGTCCTTATGTGGTCTTCATATCGCAATGATGCA

TTTGCAGGATCCCCTGGTGGTATCACTTTGACGTCTTCCTGGGATCCATCCACTGGTATTGTTTCCGACCGCACTGTG

ACAGTCACCAAGCATGATATGTTCTGCCCTGGTATCTCCATGGATGGTAACGGTCAGATCGTAGTCACAGGTGGCAAC

GATGCCAAGAAGACCAGTTTGTATGATTCATCTAGCGATAGCTGGATCCCGGGACCTGACATGCAAGTGGCTCGTGGG

TATCAGTCATCAGCTACCATGTCAGACGGTCGTGTTTTTACCATTGGAGGCTCCTGGAGCGGTGGCGTATTTGAGAAG

AATGGCGAAGTCTATAGCCCATCTTCAAAGACATGGACGTCCCTACCCAATCCCAAGGTCAACCCAATGTTGACGGCT

TABLE 8-continued (Amino acid substitutions relative to wt are in bold; DNA mutations are not highlighted.)

```
GACAAGCAAGGATTGTACCGTTCAGACAACCACGCGTGGCTCTTTGGATGGAAGAAGGGTTCGGTGTTCCAAGCGGGA

CCTAGCACAGCCATGAACTGGTACTATACCAGTGGAAGTGGTGATGTGAAGTCAGCCGGAAAACGCCAGTCTAACCGT

GGTGTAGGCCCTGATGCCATGAGCGGAAACGCTGTCATGTACCACGCCGTTAAAGGAAAGATCCTGACCTTTGGCGGC

TCCCCAGATTATCAAGACTCTGACGCCACAACCAACGCCCACATCATCACCCTCGGTGAACCCGGTACCTCTCCCAAC

ACTGTCTTTGCTAGCAATCGGTTGCACTTTGCCCGAACGTTTCACACTTCTGTTGTTCTTCCAGACGGAAACACGTTT

ATTACAGGAGGCCAACGACGTGGAATTCCGTTCGAGGATTCAACCCCGGTATTTACACCTGAGATCTACGTCCCTGAA

CAAGACACTTTCTACAAGCAGAACCCCAACTCCATTGTTCGCGCCTACCATAGCATTTCCCTTTTGTTACCTGATGGC

AGGGTATTTAACGGTGGTGGTGGTCTTTGTGGCGATTGTACCACGAATCATTTCGACGCGCAAATCTTTACGCCAAAC

TATCTTTACAATAGCAACGGCAACCTCGCGACACGTCCCAAGATTACCAGAACCTCTACACAGAGCGTCAAGGTCGGT

GGCAGAATTACAATCTCGACGGATTCTTCGATTAGCAAGGCGTCGTTGATTCGCTATGGTACAGCGACACACACGGTT

AATACTGACCAGCGCCGCATTCCCCTGACTCTGACAAACAATGGAGGAAATAGCTATTCTTTCCAAGTTCCTAGCGAC

TCTGGTGTTGCTTTGCCTGGCTACTGGATGTTGTTCGTGATGAACTCGGCCGGTGTTCCTACTGTGGCTTCGACGATT

CGCGTTACTCAGTGA
```

EXAMPLE 2

Cloning of vGO cDNA cDNAs may be sequenced directly using an AB1377 or ABI373A fluorescence-based sequencer (Perkin Elmer/Applied Biosystems Division, PE/ABD, Foster City, Calif.) and the ABI PRISM Ready Dye-Deoxy Terminator kit with Taq FS polymerase. Each ABI cycle sequencing reaction contains about 0.5 µg of plasmid DNA. Cycle-sequencing is performed using an initial denaturation at 98° C. for 1 min, followed by 50 cycles: 98° C. for 30 sec, annealing at 50° C. for 30 sec, and extension at 60° C. for 4 min. Temperature cycles and times are controlled by a Perkin-Elmer 9600 thermocycler. Extension products are purified using Centri-flex gel filtration (Advanced Genetic Technologies Corp., Gaithersburg, Md.). Each reaction product is loaded by pipette onto the column, which is then centrifuged in a swinging bucket centrifuge (Sorvall model RT6000B table top centrifuge) at 1500×g for 4 min at room temperature. Column-purified samples are dried under vacuum for about 40 min and then dissolved in 5 µl of a DNA loading solution (83% deionized formamide, 8.3 mM EDTA, and 1.6 mg/ml Blue Dextran). The samples are then heated to 90° C. for three min and loaded into the gel sample wells for sequence analysis by the ABI377 sequencer. Sequence analysis is done by importing ABI373A files into the Sequencher program (Gene Codes, Ann Arbor, Mich.). Generally, sequence reads of 700 bp are obtained. Potential sequencing errors are minimized by obtaining sequence information from both DNA strands and by re-sequencing difficult areas using primers at different locations until all sequencing ambiguities are removed.

To isolate a cDNA clone encoding full length vGO, a DNA fragment corresponding to a nucleotide sequence of the invention, or a portion thereof, can be used as a probe for hybridization screening of a phage cDNA library. The DNA fragment is amplified by the polymerase chain reaction (PCR) method. The PCR reaction mixture of 50 ml contains polymerase mixture (0.2 mM dNTPs, 1×PCR Buffer and 0.75 ml Expand High Fidelity Polymerase (Roche Biochemicals)), 1 µg of 3206491 plasmid, and 50 pmoles of forward primer and 50 pmoles of reverse primer. The primers are preferably 10 to 25 nucleotides in length and are determined by procedures well known to those skilled in the art. Amplification is performed in an Applied Biosystems PE2400 thermocycler, using the following program: 95° C. for 15 seconds, 52° C. for 30 seconds and 72° C. for 90 seconds; repeated for 25 cycles. The amplified product is separated from the plasmid by agarose gel electrophoresis, and purified by Qiaquick gel extraction kit (Qiagen).

A lambda phage library containing cDNAs cloned into lambda ZAPII phage-vector is plated with E. coli XL-1 blue host, on 15 cm LB-agar plates at a density of 50,000 pfu per plate, and grown overnight at 37° C.; (plated as described by Sambrook et al., supra). Phage plaques are transferred to nylon membranes (Amersham Hybond N.J.), denatured for 2 minutes in denaturation solution (0.5 M NaOH, 1.5 M NaCl), renatured for 5 minutes in renaturation solution (1 M Tris pH 7.5, 1.5 M NaCl), and washed briefly in 2×SSC (20×SSC: 3 M NaCl, 0.3 M Na-citrate). Filter membranes are dried and incubated at 80° C. for 120 minutes to cross link the phage DNA to the membranes.

The membranes are hybridized with a DNA probe prepared as described above. A DNA fragment (25 ng) is labeled with α-32P-dCTP (NEN) using Rediprime random priming (Amersham Pharmacia Biotech), according to manufacturers instructions. Labeled DNA is separated from unincorporated nucleotides by S200 spin columns (Amersham Pharmacia Biotech), denatured at 95° C. for 5 minutes and kept on ice. The DNA-containing membranes (above) are pre-hybridised in 50 ml ExpressHyb (Clontech) solution at 68° C. for 90 minutes. Subsequently, the labeled DNA probe is added to the hybridization solution, and the probe is left to hybridise to the membranes at 68° C. for 70 minutes. The membranes are washed five times in 2×SSC, 0.1% SDS at 42° C. for 5 minutes each, and finally washed 30 minutes in 0.1×SSC, 0.2% SDS. Filters are exposed to Kodak XAR film (Eastman Kodak Company, Rochester, N.Y., USA) with an intensifying screen at −80° C. for 16 hours. One positive colony is isolated from the plates, and replated with about 1000 pfu on a 15 cm LB plate. Plating, plaque lift to filters and hybridization are performed as described above. About four positive phage plaques are isolated form this secondary screening.

cDNA containing plasmids (pBluescript SK-) are rescued from the isolated phages by in vivo excision by culturing XL-1 blue cells co-infected with the isolated phages and with the Excision helper phage, as described by manufacturer (Stratagene). XL-blue cells containing the plasmids are plated on LB plates and grown at 37° C. for 16 hours. Colonies (18) from each plate are replated on LB plates and grown. One colony from each plate is stricken onto a nylon filter in an ordered array, and the filter is placed on a LB plate to raise the colonies. The filter is then hybridized with a labeled probe as described above. About three positive colonies are selected and grown up in LB medium. Plasmid DNA is isolated from the three clones by Qiagen Midi Kit (Qiagen) according to the manufacturer's instructions. The size of the insert is determined by digesting the plasmid with the restriction enzymes NotI and SalI, which establishes an insert size. The sequence of the entire insert is determined by automated sequencing on both strands of the plasmids.

EXAMPLE 3

Subcloning of the Coding Region of vGO via PCR

Additional experiments may be conducted to subclone the coding region of vGO and place the isolated coding region into a useful vector. Two additional PCR primers are designed based on the coding region of vGO, corresponding to either end. To protect against exonucleolytic attack during subsequent exposure to enzymes, e.g., Taq polymerase, primers are routinely synthesized with a protective run of nucleotides at the 5' end that were not necessarily complementary to the desired target.

PCR is performed in a 50 µl reaction containing 34 µl $H_2O$, 5 µl 10×TT buffer (140 mM ammonium sulfate, 0.1% gelatin, 0.6 M Tris-tricine, pH 8.4), 5 µl 15 mM $MgSO_4$, 2 µl dNTP mixture (dGTP, dATP, dTTP, and dCTP, each at 10 mM), 3 µl genomic phage DNA (0.25 µg/µl), 0.3 µl Primer 1 (1 µg/l), 0.3 µl Primer 2 (1 µg/l), 0.4 µl High Fidelity Taq polymerase (Boehringer Mannheim). The PCR reaction was started with 1 cycle of 94° C. for 2 minutes; followed by 25 cycles at 94° C. for 30 seconds, 55° C. for 30 seconds, and 72° C. for 1.3 minutes.

The contents from the PCR reaction are loaded onto a 2% agarose gel and fractionated. The DNA band of expected size is excised from the gel, placed in a GenElute Agarose spin column (Supelco) and spun for 10 minutes at maximum speed in a microfuige. The eluted DNA is precipitated with ethanol and resuspended in 6 µl $H_2O$ for ligation.

The PCR-amplified DNA fragment containing the coding region is cloned into pCR2.1 using a protocol standard in the art. In particular, the ligation reaction consists of 6 µl of VGO DNA, 1 µl 10×ligation buffer, 2 µl pCR2.1 (25 ng/µl, Invitrogen), and 1 µl T4 DNA ligase (Invitrogen). The reaction mixture is incubated overnight at 14° C. and the reaction is then stopped by heating at 65° C. for 10 minutes. Two microliters of the ligation reaction are transformed into One Shot cells (Invitrogen) and plated onto ampicillin plates. A single colony containing a recombinant pCR2.1 bearing an insert is used to inoculate a 5 ml culture of LB medium. Plasmid DNA is purified using the Concert Rapid Plasmid Miniprep System (GibcoBRL) and sequenced. Following confirmation of the sequence, a 50 ml culture of LB medium is inoculated with the transformed One Shot cells, cultured, and processed using a Qiagen Plasmid Midi Kit to yield purified pCR-VGO.

EXAMPLE 4

Recombinant Expression of vGO in Eukaryotic Host Cells

A. Expression of vGO in Mammalian Cells

To produce vGO protein, a vGO-encoding polynucleotide is expressed in a suitable host cell using a suitable expression vector and standard genetic engineering techniques. For example, the vGO-encoding sequence described in Example 1 is subcloned into the commercial expression vector pzeoSV2 (Invitrogen, San Diego, Calif.) and transfected into Chinese Hamster Ovary (CHO) cells using the transfection reagent FuGENE 6 (Boehringer-Mannheim) and the transfection protocol provided in the product insert. Other eukaryotic cell lines, including human embryonic kidney (HEK 293) and COS cells, are suitable as well. Cells stably expressing vGO are selected by growth in the presence of 100 µg/ml zeocin (Stratagene, LaJolla, Calif.). Optionally, vGO may be purified from the cells using standard chromatographic techniques. To facilitate purification, antisera is raised against one or more synthetic peptide sequences that correspond to portions of the vGO amino acid sequence, and the antisera is used to affinity purify vGO. The vGO also may be expressed in-frame with a tag sequence (e.g., polyhistidine, hemagglutinin, FLAG) to facilitate purification. Moreover, it will be appreciated that many of the uses for vGO polypeptides, such as assays described below, do not require purification of vGO from the host cell.

B. Expression of vGO in 293 Cells

For expression of vGO in mammalian cells 293 (transformed human, primary embryonic kidney cells), a plasmid bearing the relevant vGO coding sequence is prepared, using vector pSecTag2A (Invitrogen). Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants. The forward primer for amplification of this VGO cDNA is determined by routine procedures and preferably contains a 5' extension of nucleotides to introduce the HindIII cloning site and nucleotides matching the VGO sequence. The reverse primer is also determined by routine procedures and preferably contains a 5' extension of nucleotides to introduce an XhoI restriction site for cloning and nucleotides corresponding to the reverse complement of the vGO sequence. The PCR conditions are 55° C. as the annealing temperature. The PCR product is gel purified and cloned into the HindIII-XhoI sites of the vector.

The DNA is purified using Qiagen chromatography columns and transfected into 293 cells using DOTAP transfection media (Boehringer Mannheim, Indianapolis, Ind.). Transiently transfected cells are tested for expression after 24 hours of transfection, using western blots probed with antihis and anti-vGO peptide antibodies. Permanently transfected cells are selected with Zeocin and propagated. Production of the recombinant protein is detected from both cells and media by western blots probed with anti-His, anti-Myc or anti-VGO peptide antibodies.

C. Expression of vGO in COS Cells

For expression of the vGO in COS7 cells, a polynucleotide of the invention can be cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site. In addition, the plasmid contains the dhrf (dihydrofolate reductase) gene which provides selection in the presence of the drug methotrexate (MTX) for selection of stable transformants.

The forward primer is determined by routine procedures and preferably contains a 5' extension which introduces an XbaI restriction site for cloning, followed by a polynucleotide of the invention. The reverse primer is also determined by routine procedures and preferably contains 5'-extension of nucleotides which introduces a SalI cloning site followed by nucleotides which correspond to the reverse complement of a polynucleotide of the invention.

The PCR consists of an initial denaturation step of 5 min at 95° C., 30 cycles of 30 sec denaturation at 95° C, 30 sec annealing at 58 C and 30 sec extension at 72 C, followed by 5 min extension at 72° C. The PCR product is gel purified and ligated into the XbaI and SalI sites of vector p3-CI. This construct is transformed into E. coli cells for amplification and DNA purification. The DNA is purified with Qiagen chromatography columns and transfected into COS 7 cells using Lipofectamine reagent from BRL, following the manufacturer's protocols. Forty eight and 72 hours after transfection, the media and the cells are tested for recombinant protein expression.

vGO expressed from a COS cell culture can be purified by concentrating the cell-growth media to about 10 mg of protein/ml, and purifying the protein by, for example, chromatography. Purified vGO is concentrated to 0.5 mg/ml in an Amicon concentrator fitted with a YM-10 membrane and stored at −80° C.

D. Expression of vGO in Insect Cells

For expression of vGO in a baculovirus system, a polynucleotide of the invention can be amplified by PCR. The forward primer is determined by routine procedures and preferably contains a 5' extension which adds the NdeI cloning site, followed by followed by nucleotides which correspond to a polynucleotide of the invention. The reverse primer is also determined by routine procedures and preferably contains a 5' extension which introduces the KpnI cloning site, followed by followed by nucleotides which correspond to the reverse complement of a polynucleotide of the invention.

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the *Autographa californica* nuclear polyhedrosis virus (AcMNPV), and a 6XHis tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of VGO polypeptides can be used, provided that the vector construct includes appropriately located signals for transcription, translation, and trafficking, such as an in-frame AUG and a signal peptide, as required. Such vectors are described in Luckow et al., Virology 170:31–39, among others.

The virus is grown and isolated using standard baculovirus expression methods, such as those described in Summers et al. (A Manual of Methods for Baculovirus Vectors and Insect Cell Culture Procedures, Texas Agricultural Experimental Station Bulletin No. 1555 (1987)).

In a preferred embodiment, pAcHLT-A containing vGO gene is introduced into baculovirus using the "BaculoGold" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of a vGO polypeptide in a Sf9 cells, a polynucleotide of the invention can be amplified by PCR using the primers and methods described above for baculovirus expression. The vGO cDNA is cloned into vector pAcHLT-A (Pharmingen) for expression in Sf9 insect. The insert is cloned into the NdeI and KpnI sites, after elimination of an internal NdeI site (using the same primers described above for expression in baculovirus). DNA is purified with Qiagen chromatography columns and expressed in Sf9 cells. Preliminary Western blot experiments from non purified plaques are tested for the presence of the recombinant protein of the expected size which reacted with the VGO-specific antibody. These results are confirmed after further purification and expression optimization in HiG5 cells.

EXAMPLE 5

Antibodies to vGO

Standard techniques are employed to generate polyclonal or monoclonal antibodies to the vGO receptor, and to generate useful antigen-binding fragments thereof or variants thereof, including "humanized" variants. Such protocols can be found, for example, in Sambrook et al. (1989) and Harlow et al. (Eds.), *Antibodies A Laboratory Manual*; Cold Spring Harbor Laboratory; Cold Spring Harbor, N.Y. (1988). In one embodiment, recombinant vGO polypeptides (or cells or cell membranes containing such polypeptides) are used as antigen to generate the antibodies. In another embodiment, one or more peptides having amino acid sequences corresponding to an immunogenic portion of vGO (e.g., 6, 7, 8, 9, 10, 11, 12, 13, 14, 15, 16, 17, 18, 19, 20, or more amino acids) are used as antigen. Peptides corresponding to extracellular portions of vGO, especially hydrophilic extracellular portions, are preferred. The antigen may be mixed with an adjuvant or linked to a hapten to increase antibody production.

A. Polyclonal or Monoclonal Antibodies

As one exemplary protocol, recombinant vGO or a synthetic fragment thereof is used to immunize a mouse for generation of monoclonal antibodies (or larger mammal, such as a rabbit, for polyclonal antibodies). To increase antigenicity, peptides are conjugated to Keyhole Lympet Hemocyanin (Pierce), according to the manufacturer's recommendations. For an initial injection, the antigen is emulsified with Freund's Complete Adjuvant and injected subcutaneously. At intervals of two to three weeks, additional aliquots of vGO antigen are emulsified with Freund's Incomplete Adjuvant and injected subcutaneously. Prior to the final booster injection, a serum sample is taken from the immunized mice and assayed by western blot to confirm the presence of antibodies that immunoreact with vGO. Serum from the immunized animals may be used as a polyclonal antisera or used to isolate polyclonal antibodies that recognize vGO. Alternatively, the mice are sacrificed and their spleen removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mnM HEPES, pH 8.0) (Boehringer-Mannheim) is stirred into the pellet, followed by the addition of serum-free RPMI. Thereafter, the cells are centrifuged, resuspended in RPMI containing 15% FBS, 100 μM sodium hypoxanthine, 0.4 μM aminopterin, 16 μM thymidine (HAT) (Gibco), 25 units/ml IL-6 (Boehringer-Mannheim) and 1.5× $10^6$ thymocytes/ml, and plated into 10 Corning flat-bottom 96-well tissue culture plates (Corning, Corning N.Y.).

On days 2, 4, and 6 after the fusion, 100 μl of medium is removed from the wells of the fusion plates and replaced with fresh medium. On day 8, the fusions are screened by ELISA, testing for the presence of mouse IgG that binds to vGO. Selected fusion wells are further cloned by dilution until monoclonal cultures producing anti-vGO antibodies are obtained.

B. Humanization of anti-vGO Monoclonal Antibodies

The expression pattern of vGO as reported herein and the proven track record of VGOs as targets for therapeutic intervention suggest therapeutic indications for vGO inhibitors (antagonists). vGO-neutralizing antibodies comprise one class of therapeutics useful as vGO antagonists. Following are protocols to improve the utility of anti-vGO monoclonal antibodies as therapeutics in humans by "humanizing" the monoclonal antibodies to improve their serum half-life and render them less immunogenic in human hosts (i.e., to prevent human antibody response to non-human anti-vGO antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., Adv. Immunol., 44:65–92 (1989)). The variable domains of vGO-neutralizing anti-vGO antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., Nature 321:522–525 (1986); Riechmann et al., Nature 332:323–327 (1988); Verhoeyen et al., Science 239:1534–36 (1988); and Tempest et al., Bio/Technology 9:266–71 (1991)). If necessary, the β-sheet framework of the human antibody surrounding the CDR3 regions also is modified to more closely mirror the three dimensional structure of the antigen-binding domain of the original monoclonal antibody. (See Kettleborough et aL, Protein Engin., 4:773–783 (1991); and Foote et al., J. Mol. Biol., 224:487–499 (1992)).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, Molecular Immunol., 28(4/5):489–98 (1991).

The foregoing approaches are employed using vGO-neutralizing anti-vGO monoclonal antibodies and the hybridomas that produce them to generate humanized vGO-neutralizing antibodies useful as therapeutics to treat or palliate conditions wherein vGO expression or ligand-mediated vGO signaling is detrimental.

C. Human vGO-Neutralizing Antibodies from Phage Display

Human vGO-neutralizing antibodies are generated by phage display techniques such as those described in Aujame et al., Human Antibodies 8(4):155–168 (1997); Hoogenboom, TIBTECH 15:62–70 (1997); and Rader et al., Curr. Opin. Biotechnol. 8:503–508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for vGO-specific phage-antibodies using labeled or immobilized vGO as antigen-probe.

D. Human vGO-Neutralizing Antibodies from Transgenic Mice

Human vGO-neutralizing antibodies are generated in transgenic mice essentially as described in Bruggemann et al., Immunol. Today 17(8):391–97 (1996) and Bruggemann et al., Curr. Opin. Biotechnol. 8:455–58 (1997). Transgenic mice carrying human V-gene segments in germline configuration and that express these transgenes in their lymphoid tissue are immunized with a vGO composition using conventional immunization protocols. Hybridomas are generated using B cells from the immunized mice using conventional protocols and screened to identify hybridomas secreting anti-vGO human antibodies (e.g., as described above).

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention.

The entire disclosure of each publication cited herein is hereby incorporated by reference.

We claim:

1. An isolated variant galactose oxidase protein wherein said variant galactose oxidase protein differs from a wild-type galactose oxidase protein having SEQ ID NO:2 by at least one substituted amino acid, wherein said variant galactose oxidase protein has increased enzymatic activity compared to said wildtype galactose oxidase protein, and wherein the substituted amino acid is an amino acid at a position selected from the group consisting of C383, Y436, V494, Q63, S553, G6, Q238, K342, N427, and G195.

2. The protein of claim 1 wherein at least two amino acids at positions selected from the group consisting of C383, Y436, V494, Q63, S553, G6, Q238, K342, N427, and G195, are substituted with different amino acids.

3. The protein of claim 1 wherein at least three amino acids at positions selected from the group consisting of C383, Y436, V494, Q63, S553, G6, Q238, K342, N427, and G195, are substituted with different amino acids.

4. The variant galactose oxidase protein of claim 3 comprising the substitutions C383S and Y436N.

5. The variant galactose oxidase protein of claim 3 comprising the substitutions C383S, Y436H, and V494A.

6. The variant galactose oxidase protein of claim 3 comprising the substitutions C383S, Y436N, V494A, and Q63K.

7. An isolated variant galactose oxidase protein wherein said variant galactose oxidase protein differs from a wild-type galactose oxidase protein having SEQ ID NO:2 by at least one substituted amino acid, wherein said variant galactose oxidase protein has increased enzymatic activity compared to said wildtype galactose oxidase protein, and wherein said variant galactose oxidase protein has an amino acid sequence selected from the group consisting of SEQ ID NOs:3–5.

* * * * *

UNITED STATES PATENT AND TRADEMARK OFFICE
CERTIFICATE OF CORRECTION

PATENT NO.   : 6,498,026 B2
DATED        : December 24, 2002
INVENTOR(S)  : Delagrave et al.

It is certified that error appears in the above-identified patent and that said Letters Patent is hereby corrected as shown below:

Title Page,
Item [56], References Cited, OTHER PUBLICATIONS, "Foote, J., et al.," reference, please delete "franework" and insert -- framework --; please delete "thehypervariable" and insert -- the hypervariable -- therefor.
"Tempest, P.R., et al.," reference, please delete "momoclonal" and insert -- monoclonal-- therefor.

Column 18,
Line 28, please delete "Iacz" and insert -- IacZ -- therefor.
Line 40, please delete "Shine-Dalgamo" and insert -- Shine-Dalgarno -- therefor.

Column 20,
Line 31, please begin new paragraph after "immunogenicity."
Line 36, please delete "imnuunospecific" and insert -- immunospecific -- therefor.

Column 22,
Line 36, please delete "subdloned" and insert -- subcloned -- therefor.

Column 26,
Line 57, please delete "calorimetric" and insert -- colorimetric -- therefor.

Column 33,
Line 7, please delete "thermnostability" and insert -- thermostability -- therefor.

Column 34,
Line 18, please delete "thernostability" and insert -- thermostability -- therefor.

Column 41,
Line 30, please delete "subdlone" and insert -- subclone -- therefor.
Line 45, please delete the first occurrence of "(1$\mu$g/l)" and insert -- (1$\mu$g/$\mu$l) --; and delete the second occurrence of "(1$\mu$g/l)" and insert -- (1$\mu$g/$\mu$l) -- therefor.
Line 54, please delete "microfuige" and insert -- microfuge -- therefor.

Column 43 ,
Line 46, please delete the second occurrence of "followed by".
Line 50, please delete "Kpnl" and insert -- KpnI -- therefor.
Line 53, please delete "*califormica*" and insert -- *californica* -- therefor.

UNITED STATES PATENT AND TRADEMARK OFFICE
CERTIFICATE OF CORRECTION

PATENT NO. : 6,498,026 B2
DATED : December 24, 2002
INVENTOR(S) : Delagrave et al.

It is certified that error appears in the above-identified patent and that said Letters Patent is hereby corrected as shown below:

Column 45,
Line 21, please delete "mnM" and insert -- mM -- therefor.

Signed and Sealed this

Eleventh Day of January, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 3466
<212> TYPE: DNA
<213> ORGANISM: Dactylium dendroides

<400> SEQUENCE: 1

| | | | | | | |
|---|---|---|---|---|---|---|
| gaattcggca | gtgcctgtgg | atcccaatga | gagtttcaac | tagtggtgtc | ttcacgaggc | 60 |
| actgccggac | tccgtcagtc | aatagttcaa | gttagttgga | cgaaccgttg | ggccggttgg | 120 |
| tcactagacc | agggacaata | agtgcagacc | aagctgcaca | catctttgcc | aaaccactgt | 180 |
| ccatgtcaga | ccgagctgat | ataatttcag | aagcgagtga | ctcggctgca | tcttactgca | 240 |
| tttatacgag | tcctcctcag | ctgtattata | tgatctgagt | gatcatatgc | tcactggtgg | 300 |
| cgtccaatgg | ataaatactt | ctgtcacggt | ttgcttctaa | agcggtacct | tgcagatagg | 360 |
| ctggcgggta | tgcaaggacg | ggcctcggcc | ataaactttc | agctctggac | gccacttact | 420 |
| gtatgttggt | tatcgatcat | cagcgcacag | acaaatatca | gtgaattggt | tctcgtgatt | 480 |
| taagtctggc | cgccctctac | gtctaagcgg | cttcaaataa | cacgaacagg | caatttcgtt | 540 |
| tcaacgccac | aaacatttgg | gaccaattag | acaccatttt | taattcatag | ttactccgaa | 600 |
| agaagttgaa | tcagctcata | atacaaacta | gacaaggttg | tcgtgatta | tttggccctg | 660 |
| aaacgtgcag | cttttaaaac | atgatcttcc | cgcaatggcc | gatcagcaaa | cggttcttag | 720 |
| tgtatccgta | cctggatata | taagactgga | agatatcagt | tactcttcat | ctgctagtaa | 780 |
| aaccttcatc | atcttatcaa | gtcattctct | actaattatt | atctctcttt | atgtcaacat | 840 |
| gaaacacctt | ttaacactcg | ctctttgctt | cagcagcatc | aatgctgttg | ctgtcaccgt | 900 |
| ccctcacaag | gccgtaggaa | ctggaattcc | tgaagggagt | cttcagttcc | tgagccttcg | 960 |
| agcctcagca | cctatcggaa | gcgccatttc | tcgcaacaac | tgggccgtca | cttgcgacag | 1020 |
| tgcacagtcg | ggaaatgaat | gcaacaaggc | cattgatggc | aacaaggata | ccttttggca | 1080 |
| cacattctat | ggcgccaacg | gggatccaaa | gcccctcac | acatacacga | ttgacatgaa | 1140 |
| gacaactcag | aacgtcaacg | gcttgtctat | gctgcctcga | caggatggta | accaaaacgg | 1200 |
| ctggatcggt | cgccatgagg | tttatctaag | ctcagatggc | acaaactggg | gcagccctgt | 1260 |
| tgcgtcaggt | agttggttcg | ccgactctac | tacaaaatac | tccaactttg | aaactcgccc | 1320 |
| tgctcgctat | gttcgtcttg | tcgctatcac | tgaagcgaat | ggccagcctt | ggactagcat | 1380 |
| tgcagagatc | aacgtcttcc | aagctagttc | ttacacagcc | cccagcctg | gtcttggacg | 1440 |
| ctggggtccg | actattgact | taccgattgt | tcctgcggct | gcagcaattg | aaccgacatc | 1500 |
| gggacgagtc | cttatgtggt | cttcatatcg | caatgatgca | tttggaggat | ccctggtgg | 1560 |
| tatcactttg | acgtcttcct | gggatccatc | cactggtatt | gtttccgacc | gcactgtgac | 1620 |
| agtcaccaag | catgatatgt | tctgccctgg | tatctccatg | gatggtaacg | gtcagatcgt | 1680 |
| agtcacaggt | ggcaacgatg | ccaagaagac | cagtttgtat | gattcatcta | gcgatagctg | 1740 |
| gatcccggga | cctgacatgc | aagtggctcg | tgggtatcag | tcatcagcta | ccatgtcaga | 1800 |
| cggtcgtgtt | tttaccattg | gaggctcctg | gagcggtggc | gtatttgaga | agaatggcga | 1860 |
| agtctatagc | ccatcttcaa | agacatggac | gtccctaccc | aatgccaagg | tcaacccaat | 1920 |
| gttgacggct | gacaagcaag | gattgtaccg | ttcagacaac | cacgcgtggc | tctttggatg | 1980 |
| gaagaagggt | tcggtgttcc | aagcgggacc | tagcacagcc | atgaactggt | actataccag | 2040 |

```
tggaagtggt gatgtgaagt cagccggaaa acgccagtct aaccgtggtg tagcccctga   2100
tgccatgtgc ggaaacgctg tcatgtacga cgccgttaaa ggaaagatcc tgacctttgg   2160
cggctcccca gattatcaag actctgacgc acaaccaac gcccacatca tcaccctcgg    2220
tgaacccgga acatctccca acactgtctt tgctagcaat gggttgtact ttgcccgaac   2280
gtttcacacc tctgttgttc ttccagacgg aagcacgttt attacaggag ccaacgacg    2340 tggaattccg ttcgaggatt caaccccggt atttacacct gagatctacg tccctgaaca   2400
agacactttc tacaagcaga accccaactc cattgttcgc gtctaccata gcatttccct   2460
tttgttacct gatggcaggg tatttaacgg tggtggtggt ctttgtggcg attgtaccac   2520
gaatcatttc gacgcgcaaa tctttacgcc aaactatctt tacaatagca acggcaatct   2580
cgcgacacgt cccaagatta ccagaacctc tacacagagc gtcaaggtcg gtggcagaat   2640
tacaatctcg acggattctt cgattagcaa ggcgtcgttg attcgctatg gtacagcgac   2700
acacacggtt aatactgacc agcgccgcat tcccctgact ctgacaaaca atggaggaaa   2760
tagctattct ttccaagttc ctagcgactc tggtgttgct ttgcctggct actggatgtt   2820
gttcgtgatg aactcggccg gtgttcctag tgtggcttcg acgattcgcg ttactcagtg   2880
atttgttagg aagccaagtt tcataggata ttgttctact cagcgatcgg tcaatttaat   2940
ttactgccct gtttacttga agtagtcgtc gctgtaaagg gtcgccgtgt actctttctg   3000
gttgagtcaa ctcgtggtcc gtccggtcac tctgcctgtg acccagctga agactaccag   3060
aaagaagact tcaaacgtat ttcagtctag caacagcgcc aagaagctcg ctgtcaaaag   3120
tgccggtggc gtttatcgtg aatcgatagt ttgacggcct tactcgcgtc tggtgtagct   3180
ggaaaagcat caaccatccg gcccaatcac gagaatgacg tcaatggctg tgagtgatga   3240
tactaactga aaatggtaat tcaactgacg atggagcgtt cacatgctaa tcggtctcga   3300
tcatcaacag cagtaaggag cttgacggtt tgtgctctgt tgatcatcag atgatctggt   3360
gttcctgcag tagatgcaca aggccaggaa aagaagtaaa gccactttgt ctaccaatcg   3420
gttgggatgc ggtgagatct caagggaatg ggttcaagag tctaga            3466
```

<210> SEQ ID NO 2
<211> LENGTH: 639
<212> TYPE: PRT
<213> ORGANISM: Dactylium dendroides

<400> SEQUENCE: 2

```
Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
                20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
        50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
                100                 105                 110

Tyr Ser Asn Phe Glu Thr Arg Pro Ala Arg Tyr Val Arg Leu Val Ala
```

-continued

|  | 115 |  |  | 120 |  |  |  | 125 |  |  |  |
|---|---|---|---|---|---|---|---|---|---|---|---|
| Ile | Thr | Glu | Ala | Asn | Gly | Gln | Pro | Trp | Thr | Ser | Ile | Ala | Glu | Ile | Asn |
| 130 |  |  |  |  | 135 |  |  |  | 140 |  |  |  |  |  |  |

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
            165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
            195                 200                 205

Pro Ser Thr Gly Ile Val Ser Asp Arg Thr Val Thr Val Thr Lys His
210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
            245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
            275                 280                 285

Ser Trp Ser Gly Gly Val Phe Glu Lys Asn Gly Glu Val Tyr Ser Pro
290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
            325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
            355                 360                 365

Gly Lys Arg Gln Ser Asn Arg Gly Val Ala Pro Asp Ala Met Cys Gly
            370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
            405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
            435                 440                 445

Asp Gly Ser Thr Phe Ile Thr Gly Gly Gln Arg Arg Gly Ile Pro Phe
450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Val Tyr His
            485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
            515                 520                 525

Thr Pro Asn Tyr Leu Tyr Asn Ser Asn Gly Asn Leu Ala Thr Arg Pro
530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
                580                 585                 590

Thr Leu Thr Asn Asn Gly Gly Asn Ser Tyr Ser Phe Gln Val Pro Ser
            595                 600                 605

Asp Ser Gly Val Ala Leu Pro Gly Tyr Trp Met Leu Phe Val Met Asn
            610                 615                 620

Ser Ala Gly Val Pro Ser Val Ala Ser Thr Ile Arg Val Thr Gln
625                 630                 635

<210> SEQ ID NO 3
<211> LENGTH: 639
<212> TYPE: PRT
<213> ORGANISM: Artificial
<220> FEATURE:
<223> OTHER INFORMATION: Novel Sequence

<400> SEQUENCE: 3

Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
                20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
    50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
                100                 105                 110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

-continued

```
Gln Ser Ser Ala Thr Met Ser Asp Gly Arg Val Phe Thr Ile Gly Gly
        275                 280                 285

Ser Trp Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
                355                 360                 365

Gly Lys Arg Gln Ser Asn Arg Gly Val Ala Pro Asp Ala Met Ser Gly
                370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
                420                 425                 430

Asn Gly Leu His Phe Ala Arg Thr Phe His Thr Ser Val Val Leu Pro
                435                 440                 445

Asp Gly Ser Thr Phe Ile Thr Gly Gly Gln Arg Arg Gly Ile Pro Phe
                450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Pro Asp Gly Arg Val Phe Asn Gly Gly Gly
                500                 505                 510

Gly Leu Cys Gly Asp Cys Thr Thr Asn His Phe Asp Ala Gln Ile Phe
                515                 520                 525

Thr Pro Asn Tyr Leu Tyr Asn Ser Asn Gly Asn Leu Ala Thr Arg Pro
                530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Ile Pro Leu
                580                 585                 590

Thr Leu Thr Asn Asn Gly Gly Asn Ser Tyr Ser Phe Gln Val Pro Ser
                595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635
```

<210> SEQ ID NO 4
<211> LENGTH: 639
<212> TYPE: PRT
<213> ORGANISM: Artificial
<220> FEATURE:
<223> OTHER INFORMATION: Novel Sequence

<400> SEQUENCE: 4

-continued

```
Ala Ser Ala Pro Ile Gly Ser Ala Ile Ser Arg Asn Asn Trp Ala Val
  1               5                  10                 15

Thr Cys Asp Ser Ala Gln Ser Gly Asn Glu Cys Asn Lys Ala Ile Asp
             20                  25                 30

Gly Asn Lys Asp Thr Phe Trp His Thr Phe Tyr Gly Ala Asn Gly Asp
             35                  40                 45

Pro Lys Pro Pro His Thr Tyr Thr Ile Asp Met Lys Thr Thr Lys Asn
 50              55                  60

Val Asn Gly Leu Ser Met Leu Pro Arg Gln Asp Gly Asn Gln Asn Gly
 65              70                  75                 80

Trp Ile Gly Arg His Glu Val Tyr Leu Ser Ser Asp Gly Thr Asn Trp
                 85                  90                 95

Gly Ser Pro Val Ala Ser Gly Ser Trp Phe Ala Asp Ser Thr Thr Lys
                100                 105                110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                160

Trp Gly Pro Thr Ile Asp Leu Pro Ile Val Pro Ala Ala Ala Ile
                165                 170                 175

Glu Pro Thr Ser Gly Arg Val Leu Met Trp Ser Ser Tyr Arg Asn Asp
                180                 185                 190

Ala Phe Ala Gly Ser Pro Gly Gly Ile Thr Leu Thr Ser Ser Trp Asp
            195                 200                 205

Pro Ser Thr Gly Ile Val Ser Asp Arg Thr Val Thr Val Thr Lys His
        210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Trp Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
            355                 360                 365

Gly Lys Arg Gln Ser Asn Arg Gly Val Ala Pro Asp Ala Met Ser Gly
        370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415
```

Ile Thr Leu Gly Glu Pro Gly Thr Ser Pro Asn Thr Val Phe Ala Ser
            420                 425                 430

Asn Gly Leu His Phe Ala Arg Thr Phe His Thr Ser Val Val Leu Pro
            435                 440                 445

Asp Gly Ser Thr Phe Ile Thr Gly Gly Gln Arg Arg Gly Ile Pro Phe
            450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
            485                 490                 495

Ser Ile Ser Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
            515                 520                 525

Thr Pro Asn Tyr Leu Tyr Asn Ser Asn Gly Asn Leu Ala Thr Arg Pro
            530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
            565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
            595                 600                 605

Asp Ser Gly Val Ala Leu Pro Gly Tyr Trp Met Leu Phe Val Met Asn
            610                 615                 620

Ser Ala Gly Val Pro Ser Val Ala Ser Thr Ile Arg Val Thr Gln
625                 630                 635

<210> SEQ ID NO 5
<211> LENGTH: 639
<212> TYPE: PRT
<213> ORGANISM: Artificial
<220> FEATURE:
<223> OTHER INFORMATION: Novel Sequence

<400> SEQUENCE: 5

Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
            50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
            85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
            130                 135                 140

```
Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ile
            165                 170                 175

Glu Pro Thr Ser Gly Arg Val Leu Met Trp Ser Ser Tyr Arg Asn Asp
                180                 185                 190

Ala Phe Gly Gly Ser Pro Gly Gly Ile Thr Leu Thr Ser Ser Trp Asp
                195                 200                 205

Pro Ser Thr Gly Ile Val Ser Asp Arg Thr Val Thr Val Thr Lys His
            210                 215                 220

Asp Met Phe Cys Pro Gly Ile Ser Met Asp Gly Asn Gly Gln Ile Val
225                 230                 235                 240

Val Thr Gly Gly Asn Asp Ala Glu Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Trp Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Ser
                340                 345                 350

Ala Met Asn Trp Tyr Tyr Thr Ser Gly Ser Gly Asp Val Arg Ser Ala
        355                 360                 365

Gly Lys Arg Gln Ser Asn Arg Gly Val Ala Pro Asp Ala Met Ser Gly
    370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu His Phe Ala Arg Thr Phe His Thr Ser Val Val Leu Pro
        435                 440                 445

Asp Gly Ser Thr Phe Ile Thr Gly Gly Gln Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
                500                 505                 510

Gly Leu Cys Gly Asp Cys Thr Thr Asn His Phe Asp Ala Gln Ile Phe
            515                 520                 525

Thr Pro Asn Tyr Leu Tyr Asn Ser Asn Gly Asn Leu Ala Thr Arg Pro
            530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
```

|     |     |     | 565 |     |     |     | 570 |     |     |     | 575 |     |
|-----|-----|-----|-----|-----|-----|-----|-----|-----|-----|-----|-----|-----|

Gly Thr Ala Thr His Thr Val Asn Thr Asp Gln Arg Arg Ile Pro Leu
            580             585             590

Thr Leu Thr Asn Asn Gly Gly Asn Ser Tyr Ser Phe Gln Val Pro Ser
        595             600             605

Asp Ser Gly Val Ala Leu Pro Gly Tyr Trp Met Leu Phe Val Met Asn
    610             615             620

Ser Ala Gly Val Pro Ser Val Ala Ser Thr Ile Arg Val Thr Gln
625             630             635

<210> SEQ ID NO 6
<211> LENGTH: 2046
<212> TYPE: DNA
<213> ORGANISM: Artificial
<220> FEATURE:
<223> OTHER INFORMATION: Novel Sequence

<400> SEQUENCE: 6

```
atgaaacacc ttttaacact cgctctttgc ttctcgagca tcaatgctgt tgctgtcacc      60
gtccctcaca aggccgtagg aactggaatt cctgaaggga gtcttcagtt cctgagcctt     120
cgagcctcag cacctatcgg aagcgccatt tctcgcaaca actgggccgt cacttgcgac     180
agtgcacagt cgggaaatga atgcaacaag gccattgatg caacaaggga tacctttttgg    240
cacacattct atggcgccaa cggggatcca agccccctc acacatacac gattgacatg      300
aagacaacta agaacgtcaa cggcttgtct atgctgcctc gacaggatgg taaccaaaac    360
ggctggatcg tcgccatga ggtttatcta agctcagatg gcacaaactg gggcagccct    420
gttgcgtcag gtagttggtt cgccgactct actacaaaat actccaactt tgaaactcgc    480
cctgctcgct atgttcgtct tgtcgctatc actgaagcga atggccagcc ttggactagc    540
attgcagaga tcaacgtctt ccaagctagt tcttacacag cccccagcc tggtcttgga    600
cgctgggtc cgactattga cttaccgatt gttcctgcgg ctgcagcaat tgaaccgaca    660
tcgggacgag tccttatgtg gtcttcatat cgcaatgatg catttgcagg atccctggt     720
ggtatcactt tgacgtcttc ctgggatcca tccactggta ttgtttccga ccgcactgtg    780
acagtcacca agcatgatat gttctgccct ggtatctcca tggatggtaa cggtcagatc    840
gtagtcacag gtggcaacga tgccaagaag accagtttgt atgattcatc tagcgatagc    900
tggatcccgg gacctgacat gcaagtggct cgtgggtatc agtcatcagc taccatgtca    960
gacggtcgtg ttttttaccat tggaggctcc tggagcggtg gcgtatttga agaatggc     1020
gaagtctata gcccatcttc aaagacatgg acgtccctac ccaatgccaa ggtcaaccca   1080
atgttgacgg ctgacaagca aggattgtac cgttcagaca ccacgcgtg gctctttgga   1140
tggaagaagg gttcggtgtt ccaagcggga cctagcacag ccatgaactg gtactatacc   1200
agtggaagtg gtgatgtgaa gtcagccgga aaacgccagt ctaaccgtgg tgtagcccct   1260
gatgccatga gcggaaacgc tgtcatgtac gacgccgtta aggaaagat cctgaccttt   1320
ggcggctccc cagattatca agactctgac gccacaacca acgcccacat catcaccctc   1380
ggtgaacccg gtacctctcc caacactgtc tttgctagca atgggttgca ctttgcccga   1440
acgtttcaca cttctgttgt tcttccagac ggaagcacgt ttattacagg aggccaacga   1500
cgtggaattc cgttcgagga ttcaaccccg gtattacac ctgagatcta cgtccctgaa    1560
caagacactt tctacaagca gaaccccaac tccattgttc gcgcctacca tagcatttcc   1620
cttttgttac ctgatggcag ggtatttaac ggtggtggtg gtctttgtgg cgattgtacc   1680
```

-continued

```
acgaatcatt tcgacgcgca aatctttacg ccaaactatc tttacaatag caacggcaac    1740
ctcgcgacac gtcccaagat taccagaacc tctacacaga gcgtcaaggt cggtggcaga    1800
attacaatct cgacggattc ttcgattagc aaggcgtcgt tgattcgcta tggtacagcg    1860
acacacacgg ttaatactga ccagcgccgc attccctga ctctgacaaa caatggagga     1920
aatagctatt ccttccaagt tcctagcgac tctggtgttg ctttgcctgg ctactggatg    1980
ttgttcgtga tgaactcggc cggtgttcct agtgtggctt cgacgattcg cgttactcag    2040
tgataa                                                               2046
```

<210> SEQ ID NO 7
<211> LENGTH: 2046
<212> TYPE: DNA
<213> ORGANISM: Artificial
<220> FEATURE:
<223> OTHER INFORMATION: Novel Sequence

<400> SEQUENCE: 7

```
atgaaacacc ttttaacact cgctctttgc ttctcgagca tcaatgctgt tgctgtcacc      60
gtccctcaca aggccgtagg aactggaatt cctgaaggga gtcttcagtt cctgagcctt     120
cgagcctcag cacctatcgg aagcgccatt tctcgcaaca actgggccgt cacttgcgac     180
agtgcacagt cgggaaatga atgcaacaag gccattgatg caacaaagga tacctttggg    240
cacacattct atggcgccaa cggggatcca agcccctc acacatacac gattgacatg       300
aagacaactc agaacgtcaa cggcttgtct atgctgcctc gacaggatgg taaccaaaac    360
ggctggatcg gtcgccatga ggtttatcta agctcagatg cacaaactg ggcagccct      420 gttgcgtcag gtagttggtt cgccgactct actacaaaat actccaactt tgaaactcgc    480
cctgctcgct atgttcgtct tgtcgctatc actgaagcga atggccagcc ttggactagc    540
attgcagaga tcaacgtctt ccaagctagt tcttacacag ccccccagcc tggtcttgga    600
cgctggggtc cgactattga cttaccgatt gttcctgcgg ctgcagcaat tgaaccgaca    660
tcgggacgag tccttatgtg gtcttcatat cgcaatgatg catttggagg atcccctggt    720
ggtatcactt tgacgtcttc ctgggatcca tccactggta ttgtttccga ccgcactgtg    780
acagtcacca agcatgatat gttctgccct ggtatctcca tggatggtaa cggtcagatc    840
gtagtcacag gtggcaacga tgccgagaag accagtttgt atgattcatc tagcgatagc    900
tggatcccgg gacctgacat gcaagtggct cgtgggtatc agtcatcagc taccatgtca    960
gacggtcgtg ttttttaccat tggaggctcc tggagcggtg gcgtatttga agaatggc    1020 gaagtctata gcccatcttc aaagacatgg acgtccctac ccaatgccaa ggtcaaccca    1080
atgttgacgg ctgacaagca aggattgtac cgttcagaca accacgcgtg gctctttgga    1140
tggaagaagg gttcggtgtt ccaagcggga cctagctcag ccatgaactg gtactatacc    1200
agtggaagtg gtgatgtgag gtcagccgga aaacgccagt ctaaccgtgg tgtagcccct    1260
gatgccatga gcggaaacgc tgtcatgtac gacgccgtta aggaaagat cctgaccttt     1320 ggcggctccc cagattatca agactctgac gccacaacca acgcccacat catcaccctc    1380
ggtgaacccg gtacctctcc caacactgtc tttgctagca tgggttgca cttttgcccga   1440 acgtttcaca cctctgttgt tcttccagac ggaagcacgt ttattacagg aggccaacga    1500
cgtggaattc cgttcgagga ttcaaccccg gtatttacac ctgagatcta cgtccctgaa    1560
caagacactt tctacaagca gaaccccaac tccattgttc gcgcctacca tagcatttcc    1620
```

-continued

| | |
|---|---|
| cttttgttac ctgatggcag ggtatttaac ggtggtggtg gtctttgtgg cgattgtacc | 1680 |
| acgaatcatt tcgacgcgca aatctttacg ccaaactatc tttacaatag caacggcaac | 1740 |
| ctcgcgacac gtcccaagat taccagaacc tctacacaga gcgtcaaggt cggtggcaga | 1800 |
| attacaatct cgacggattc ttcgattagc aaggcgtcgt tgattcgcta tggtacagcg | 1860 |
| acacacacgg ttaatactga ccagcgccgc attcccctga ctctgacaaa caatggagga | 1920 |
| aatagctatt ctttccaagt tcctagcgac tctggtgttg ctttgcctgg ctactggatg | 1980 |
| ttgttcgtga tgaactcggc cggtgttcct agtgtggctt cgacgattcg cgttactcag | 2040 |
| tgataa | 2046 |

<210> SEQ ID NO 8
<211> LENGTH: 2043
<212> TYPE: DNA
<213> ORGANISM: Artificial
<220> FEATURE:
<223> OTHER INFORMATION: Novel Sequence

<400> SEQUENCE: 8

| | |
|---|---|
| atgaaacacc ttttaacact cgtctttgc ttctcgagca tcaatgctgt tgctgtcacc | 60 |
| gtccctcaca aggccgtagg aactggaatt cctgaaggga gtcttcagtt cctgagcctt | 120 |
| cgagcctcag cacctatcgg aagcgccatt tctcgcaaca actgggccgt cacttgcgac | 180 |
| agtgcacagt cggaaatgga atgcaacaag gccattgatg caacaaggga taccttttgg | 240 |
| cacacattct atggcgccaa cggggatcca agccccctc acacatacac gattgacatg | 300 |
| aagacaactc agaacgtcaa cggcttgtct atgctgcctc gacaggatgg taaccaaaac | 360 |
| ggctggatcg gtcgccatga ggtttatcta agctcagatg cacaaactg ggcagcccct | 420 |
| gttgcgtcag gtagttggtt cgccgactct actacaaaat actccaactt gaaactcgc | 480 |
| cctgctcgct atgttcgtct gtcgctatc actgaagcga atggccagcc ttggactagc | 540 |
| attgcagaga tcaacgtctt ccaagctagt tcttacacag cccccagcc tggtcttgga | 600 |
| cgctggggtc cgactattga cttaccgatt gttcctgcgg ctgcagcaat tgaaccgaca | 660 |
| tcgggacgag tccttatgtg gtcttcatat cgcaatgatg catttggagg atcccctggt | 720 |
| ggtatcactt tgacgtcttc ctgggatcca tccactggta ttgtttccga ccgcactgtg | 780 |
| acagtcacca agcatgatat gttctgccct ggtatctcca tggatggtaa cggtcagatc | 840 |
| gtagtcacag gtggcaacga tgccaagaag accagtttgt atgattcatc tagcgatagc | 900 |
| tggatcccgg gacctgacat gcaagtggct cgtgggtatc agtcatcagc taccatgtca | 960 |
| gacggtcgtg tttttaccat tggaggctcc tggagcggtg gcgtatttga aagaatggc | 1020 |
| gaagtctata gcccatcttc aaagacatgg acgtccctac ccaatgccaa ggtcaaccca | 1080 |
| atgttgacgc tgacaagca aggattgtac cgttcagaca ccacgcgtg gctctttgga | 1140 |
| tggaagaagg gttcggtgtt ccaagcggga cctagcacag ccatgaactg gtactatacc | 1200 |
| agtggaagtg gtgatgtgaa gtcagccgga aaacgccagt ctaaccgtgg tgtagcccct | 1260 |
| gatgccatga gcggaaacgc tgtcatgtac gacgccgtta aggaaagat cctgaccttt | 1320 |
| ggcggctccc cagattatca agactctgac gccacaacca acgccacat catcaccctc | 1380 |
| ggtgaacccg gtacctctcc caacactgtc tttgctagca atgggttgca ctttgcccga | 1440 |
| acgtttcaca cttctgttgt tcttccagac ggaagcacgt ttattacagg aggccaacga | 1500 |
| cgtggaattc cgttcgagga ttcaacccg gtatttacac ctgagatcta cgtccctgaa | 1560 |
| caagacactt tctacaagca gaaccccaac tccattgttc gcgcctacca tagcatttcc | 1620 |

```
cttttgttac ctgatggcag ggtatttaac ggtggtggtg gtctttgtgg cgattgtacc    1680
acgaatcatt tcgacgcgca aatctttacg ccaaactatc tttacaatag caacggcaac    1740
ctcgcgacac gtcccaagat taccagaacc tctacacaga gcgtcaaggt cggtggcaga    1800
attacaatct cgacggattc ttcgattagc aaggcgtcgt tgattcgcta tggtacagcg    1860
acacacacgg ttaatactga ccagcgccgc attcccctga ctctgacaaa caatggagga    1920
aatagctatt ctttccaagt tcctagcgac tctggtgttg ctttgcctgg ctactggatg    1980
ttgttcgtga tgaactcggc cggtgttcct agtgtggctt cgacgattcg cgttactcag    2040
tga                                                                  2043
```